US009446185B2

(12) United States Patent (10) Patent No.: US 9,446,185 B2
Yodfat et al. (45) Date of Patent: Sep. 20, 2016

(54) DEVICES AND METHODS FOR IMPROVING ACCURACY OF FLUID DELIVERY

(75) Inventors: Ofer Yodfat, Modi'in (IL); Avihoo P. Keret, Kfar Vradim (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 354 days.

(21) Appl. No.: 12/921,702

(22) PCT Filed: Mar. 12, 2009

(86) PCT No.: PCT/IL2009/000288
§ 371 (c)(1),
(2), (4) Date: Sep. 9, 2010

(87) PCT Pub. No.: WO2009/113075
PCT Pub. Date: Sep. 17, 2009

(65) Prior Publication Data
US 2011/0034900 A1 Feb. 10, 2011

Related U.S. Application Data

(60) Provisional application No. 61/069,297, filed on Mar. 12, 2008.

(51) Int. Cl.
*A61M 5/142* (2006.01)
*A61M 5/168* (2006.01)
*F04B 43/12* (2006.01)

(52) U.S. Cl.
CPC ..... *A61M 5/14232* (2013.01); *A61M 5/14248* (2013.01); *A61M 5/16804* (2013.01);
(Continued)

(58) Field of Classification Search
CPC .................. A61M 5/14232; A61M 5/14248; A61M 5/16804; A61M 5/16831; A61M 5/16877; A61M 2205/50
See application file for complete search history.

(56) References Cited

U.S. PATENT DOCUMENTS 4,568,255 A    2/1986  Lavender et al.
5,531,680 A *  7/1996  Dumas .................. A61M 5/142
                                                    417/474

(Continued)

FOREIGN PATENT DOCUMENTS

EP    1 769 815 A1    4/2007
EP    1 834 658 A1    9/2007

(Continued)

OTHER PUBLICATIONS

International Search Report, PCT Application No. PCT/IL2009/000288, date of mailing Aug. 4, 2009 (4 pgs.).

*Primary Examiner* — Emily Schmidt
*Assistant Examiner* — Lauren M Peng
(74) *Attorney, Agent, or Firm* — Dinsmore & Shohl LLP

(57) ABSTRACT

Devices and methods for delivering therapeutic fluid to a patient's body are described. The devices may comprise a dispensing unit having a reservoir, a driving mechanism having a movable member for delivering therapeutic fluid to a patient's body, at least one sensor for sensing a relative position of the movable member and generating a signal, and a processor for controlling the driving mechanism to deliver an amount of therapeutic fluid that compensates for a change in the flow of the therapeutic fluid occurring during fluid delivery. The methods may be implemented by operating the driving mechanism, receiving a signal based on the position of the movable member, determining an amount of therapeutic fluid to deliver, and controlling the driving mechanism to deliver an amount of fluid that compensates for a change in flow occurring during fluid delivery.

25 Claims, 27 Drawing Sheets

(52) U.S. Cl.
CPC ..... *A61M5/16831* (2013.01); *A61M 5/16877* (2013.01); *F04B 43/1253* (2013.01); *A61M 2205/50* (2013.01)

(56) References Cited

U.S. PATENT DOCUMENTS

| | | | |
|---|---|---|---|
| 5,720,721 A * | 2/1998 | Dumas et al. | 604/67 |
| 5,791,880 A * | 8/1998 | Wilson | A61M 5/14232 |
| | | | 417/14 |
| 6,099,272 A | 8/2000 | Armstrong et al. | |
| 6,203,528 B1 * | 3/2001 | Deckert | A61M 5/142 |
| | | | 604/131 |
| 6,854,620 B2 * | 2/2005 | Ramey | A61M 5/1456 |
| | | | 222/153.13 |
| 2003/0031590 A1 | 2/2003 | Park | |
| 2007/0073235 A1 * | 3/2007 | Estes | A61M 5/14244 |
| | | | 604/151 |
| 2007/0106218 A1 | 5/2007 | Yodfat et al. | |
| 2008/0215035 A1 | 9/2008 | Yodfat et al. | |
| 2011/0160697 A1 * | 6/2011 | Yodfat et al. | 604/506 |
| 2011/0172594 A1 * | 7/2011 | Yodfat et al. | 604/67 |

FOREIGN PATENT DOCUMENTS

| | | |
|---|---|---|
| GB | 2 207 196 A | 1/1989 |
| WO | WO 02/068015 A2 | 9/2002 |
| WO | WO 02/068015 A3 | 9/2002 |
| WO | WO 03/097120 A2 | 11/2003 |
| WO | WO 03/097120 A3 | 11/2003 |
| WO | WO 2007/052277 A1 | 5/2007 |
| WO | WO 2008/012817 A1 | 1/2008 |
| WO | WO 2008/139458 A2 | 11/2008 |
| WO | WO 2008/139458 A3 | 11/2008 |
| WO | WO 2008/139459 A1 | 11/2008 |
| WO | WO-2009125398 A2 | 10/2009 |

* cited by examiner

DEVICES AND METHODS FOR IMPROVING ACCURACY OF FLUID DELIVERY

CROSS-REFERENCE TO RELATED APPLICATIONS

The present application is a 35 U.S.C. §371 national stage entry of PCT/IL2009/000288, which has an international filing date of Mar. 12, 2009 and claims priority to U.S. Provisional Patent Application No. 61/069,297, filed in the U.S. Patent & Trademark Office on Mar. 12, 2008. The present application incorporates herein by reference the disclosure of each of the above-referenced applications in its entirety.

FIELD

Devices and methods for sustained medical infusion of fluids are described herein. In particular, an ambulatory infusion device that can be attached to the patient's body and dispense accurate doses of fluids to the patient's body is provided. More particularly, a skin adherable infusion device that may employ a peristaltic metering mechanism and a method for improving fluid delivery accuracy are described herein. The term "fluid" refers to any therapeutic fluid, including but not limited to insulin.

BACKGROUND

Medical treatment of several illnesses requires continuous drug infusion into various body compartments via subcutaneous or intra-venous injections. Diabetes mellitus patients, for example, require administration of varying amounts of insulin throughout the day to control their blood glucose levels. In recent years, ambulatory insulin infusion pumps have emerged as a superior alternative to multiple daily syringe injections of insulin. These pumps, which deliver insulin at a continuous basal rate as well as in bolus volumes, were developed to liberate patients from repeated self-administered injections, and allow them to maintain almost normal routines. Delivered volumes must be precise and in accordance with a programmed delivery schedule because an overdose or under-dose of insulin could be fatal.

Several conventional ambulatory insulin infusion devices are currently available on the market. One configuration of these devices relates to a miniature skin adherable infusion device, also referred to as a "dispensing patch". It is lightweight, small in size (discreet), and has no tubing. Some dispensing patches use peristaltic metering mechanisms. An example of such a dispensing patch is disclosed in the co-owned, co-pending U.S. patent application Ser. No. 11/397,115 and International Patent Application No. PCT/IL06/001276, the disclosures of which are incorporated herein by reference in their entireties. Other dispensing patches may employ syringe pumps, examples of which are disclosed in co-owned, co-pending International Patent Application No. PCT/IL2008/000641, filed May 11, 2008 and entitled "A Positive Displacement Pump" and U.S. Provisional Patent Application No. 61/123,509, filed Apr. 9, 2008 and entitled "Systems, Devices and Methods for Fluid Delivery", the disclosures of which are incorporated herein by reference in their entireties.

A peristaltic mechanism typically includes a rotary wheel with rollers and a flexible delivery tube. The rotary wheel with rollers periodically squeezes the flexible tube and delivers the fluid in the direction of rotation of the rotary wheel. A stator provides a counter force against the rotary wheel and has a groove designed to hold the tube in place. The spring-loaded stator can change its position in relation to the rotary wheel. A revolution counter alerts the patient in cases of electro-mechanical dissociation, as disclosed in the co-owned, co-pending International Patent Application No. PCT/IL08/000,642, filed May 11, 2008, and entitled "Methods and Apparatus for Monitoring Rotation of an Infusion Pump Driving Mechanism," the disclosure of which is incorporated herein by reference in its entirety.

The use of a peristaltic mechanism maintains fluid sterility because the rotary wheel only touches the outer surface of the delivery tube, avoids pressure fluctuations because the delivery tube is continuously squeezed, and eliminates the need for a check valve.

Typically, an accurate and constant flow rate is to be delivered into the body of a user. However, some pumping mechanisms, such as a peristaltic pumping mechanism, have a variable flow rate, thus limiting the pumping mechanism as applied to ambulatory insulin infusion pumps. The peristaltic mechanism delivers the fluid in a series of pulses or surges, also referred to as a pulsation. During a rotary wheel cycle, the flow rate changes according to the relative position of the rollers and the stator. Moreover, no flow or backflow occurs when each roller disengages the stator. These pulsations are of no consequence to most applications, but their influence is significant when a low flow rate is needed, such as for example, during basal insulin delivery by a portable pump. The pulsation frequency is equal to the frequency of passing of successive rollers in contact with the delivery tube causing to a variable ratio between the amount of fluid delivered and the relative position of the pumping mechanism. This may cause inaccuracies and variation, especially when the pumping mechanism is activated without completing a full period, such as for example during low basal delivery. And when the dispensing device is operated according to the pumping mechanism periods, the ability to control and program the fluid delivery schedule is reduced and the effectiveness of the therapeutic treatment may be hampered. Referring to a peristaltic pumping mechanism as an example, the volume delivered by the change of the relative position of the rotary wheel (also referred to as a "flow rate") may be affected by various parameters, including the delivery tube's mechanical characteristics (e.g., inner and outer diameters and polymer characterization), the rotary wheel diameter, the number of rollers, the stator's diameter, and the stator's spring. The flow rate can also be influenced by other moving parts of the peristaltic pumping mechanism, including without limitation, gears, the shaft, the motor, the steady stator, and the spring-loaded stator.

Conventional systems use mechanical means to reduce pulsations. An example of such mechanical means is discussed in U.S. Pat. No. 6,099,272 to Armstrong et al., which discloses a torque control cam that increases the minimal torque provided by the pump. In addition, U.S. Pat. No. 4,568,255 to Lavender et al. discloses elongated sloped-sweep vanes that increase pressure on the tube. Both mechanisms require high energy, a large motor and a powerful battery.

The reliability of an infusion pump can be enhanced by monitoring the flow rate of the therapeutic fluid. Conventional flow meters employed in infusion pumps are heavy and bulky and cannot precisely monitor low flow volumes. In other words, they do not allow accurate monitoring of the flow rate. An example of such a measurement mechanism is disclosed in International Patent Application No. PCT/US2002/038822 to Sage et al., wherein flow is monitored by optically detecting changes of the fluid refraction index caused by artificially-induced heat. This method is inaccurate for monitoring low flow rates and therefore cannot prevent potential deterioration of the therapeutic fluid or other fluid delivered to the body.

SUMMARY

Devices and methods that may employ a pumping mechanism (e.g., peristaltic pump or syringe pump) having a dispensing unit and means for monitoring and controlling the volume of therapeutic fluid being delivered are disclosed. In some embodiments, the dispensing unit may secured to the user's body (e.g., skin adherable). The dispensing unit may be composed of two parts: a disposable part and a reusable part. The dispensing unit may include one or more monitoring means for determining and providing the relative position of one or more movable components of the dispensing unit. A movable component may include but is not limited to a motor, gear, shaft, rotary wheel, roller, plunger, encoder, stator, or cogwheel. A sensor may be positioned on at least one movable component and may include an encoder wheel, at least one light-emitting source (e.g., a light-emitting diode, or LED), and at least one light detector. There is also provided a processor that receives one or more sensor inputs and controls a motor in accordance with those inputs (i.e., closed-loop feedback) to deliver the required dosage accurately. In some embodiments, the motor is activated to compensate for inaccuracies in the pumping mechanism that result from changing a variable pumping rate to a constant flow rate. In particular, inaccuracies may be caused by pulsations in a peristaltic pumping mechanism, asymmetric components (e.g. gear) or plunger wobble in a syringe pumping mechanism. In some embodiments, the processor can be programmed to compensate for a change in the flow rate. The compensation can be calculated accurately by determining and analyzing the amount of fluid delivered with each displacement of a wheel (e.g., rotation of a rotary wheel, cog wheel, or encoder wheel) or of a plunger or other movable components in various other positive displacement pumps. The change in the flow rate, or the compensation, may correlate to the relative position of the one or more movable components as determined by a sensor.

In some embodiments, the flow rate may vary according to the rotation of a wheel (e.g., a rotary wheel, cog wheel, or encoder wheel). In some embodiments, the compensation may be related to a partial wheel rotation. In some embodiments, the amount of fluid delivered may depend on the initial and final positions of the pumping mechanism and on variable flow parameters.

In some embodiments, the processor can be programmed to compensate for backflow caused by the pulsation of a peristaltic pumping mechanism. The compensation can be calculated accurately by determining and analyzing the amount of fluid delivered with each rotation of a wheel. The compensation may correlate to the position of the wheel's roller relative to the stator. Some embodiments may include simplified adjustments to the number of motor rotations (e.g., every ten full motor rotations require another half rotation).

The fluid delivery device may also include a cradle unit, a cannula cartridge unit (that may be skin adherable), and a remote control unit. In some embodiments, the remote control unit may be a cellular phone, a watch, a personal digital assistance (PDA), an iPod, or any other suitable device. In some embodiments, the cradle unit enables connection and disconnection of the dispensing unit from the user's body.

Some embodiments relate to a portable dispensing unit and a method for monitoring and controlling the flow of the therapeutic fluid being delivered.

Some embodiments relate to a portable dispensing unit that employs a peristaltic mechanism and a feedback control for minimizing pulsation, as well as correction in a situation when there is no flow or backflow.

Some embodiments relate to a portable dispensing unit that employs a peristaltic mechanism and a method for preventing or at least minimizing the occurrence of pulsations, no flow or backflow.

Some embodiments relate to controlling and monitoring the relative position between movable components and steady components of the dispensing unit. More particularly, some embodiments relate to controlling and monitoring the relative angular position between rotating components and steady components of the dispensing unit (i.e., rollers and stator, cogwheels and chassis).

Some embodiments relate to monitoring the amount of delivered fluid by controlling the relative position of movable components.

In some embodiments, the position of the movable components within the pumping mechanism may be sensed by displacement transducers, optical sensors, load cell sensors, capacitive sensing, magnetic sensors, piezoelectric sensors, spring potentiometers, or rotary sensors. In some embodiments, the dispensing unit may include more than one sensor. In some embodiments, position can be sensed continuously or at predetermined phases of the pumping mechanism cycle.

In some embodiments, the amount of delivered fluid is calculated according to the two consecutive positions of the pumping mechanism defining an interval, which are determined according to sensor signals, and determining the amount of fluid delivered during a first portion of the interval and during a second portion of the interval. In some embodiments, the interval is related to the pumping mechanism period. In some embodiments, the ratio between the first portion and the amount of fluid delivered may differ from the ratio between the second portion and the amount of fluid delivered.

DETAILED DESCRIPTION

Figure 1A:
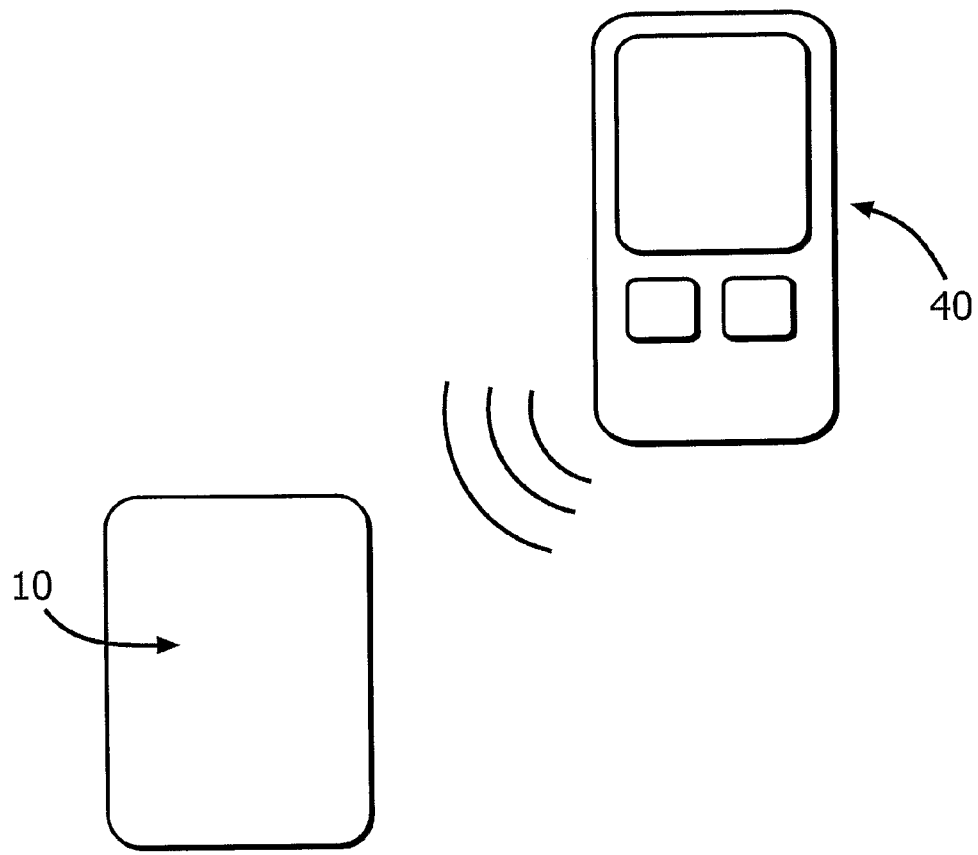
FIGS. 1a-c illustrate a fluid dispensing device configured as a single-part or two-part dispensing unit and an optional remote control unit according to some embodiments.
Figure 1B:
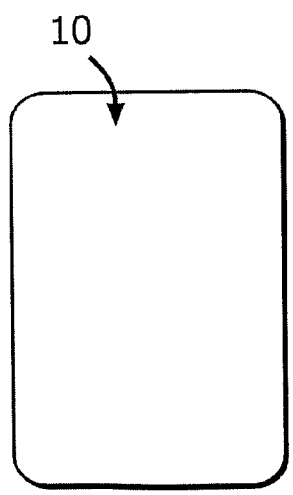
Figure 1C:
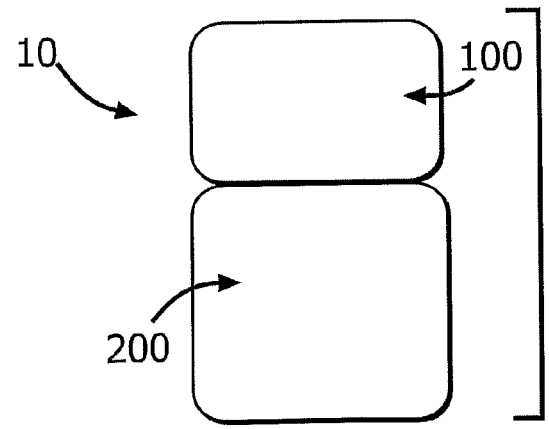

FIG. 1a illustrates a schematic diagram of fluid delivery device having a dispensing unit (10) and a remote control unit (40). In some embodiments, the dispensing unit (10) can be composed of a single part (FIG. 1b) or two parts (FIG. 1c). The two-part dispensing unit (10) includes a reusable part (100) and a disposable part (200). In some embodiments, the dispensing unit (10) can be adhered to the body of the patient, i.e., the user of the dispensing unit (10). In some embodiments, the dispensing unit (10) can be located remotely from the patient's body (i.e., not adhered directly or indirectly to the patient's body). Some embodiments may use the remote control unit (40) to control the dispensing of fluid to the patient via the dispensing unit (10), whether the dispensing unit (10) is adhered to the patient's body or located remotely away from the patient's body. In some embodiments, the dispensing unit (10) can be used with a cradle unit (not shown), as disclosed in co-owned, co-pending U.S. patent application Ser. No. 12/004,837, filed on Dec. 20, 2007, and entitled "Systems, Devices and Methods for Sustained Delivery of a Therapeutic Fluid," the disclosure of which is incorporated herein by reference in its entirety. The dispensing unit (10) can be connected and disconnected from the cradle unit. The remote control unit (40) can be a cellular telephone, a watch, a PDA, an iPod, or any other suitable device. The cradle unit can be skin adherable. In some embodiments, the fluid delivery device can also include a cannula cartridge unit (not shown). In some embodiments, the dispensing unit (10) can be a patch-like device securable to the user (e.g., skin adherable). In some embodiments, the dispensing unit (10) has a portion that is connectable to the user directly (adhered) or indirectly (by a cradle).

Figure 2A:
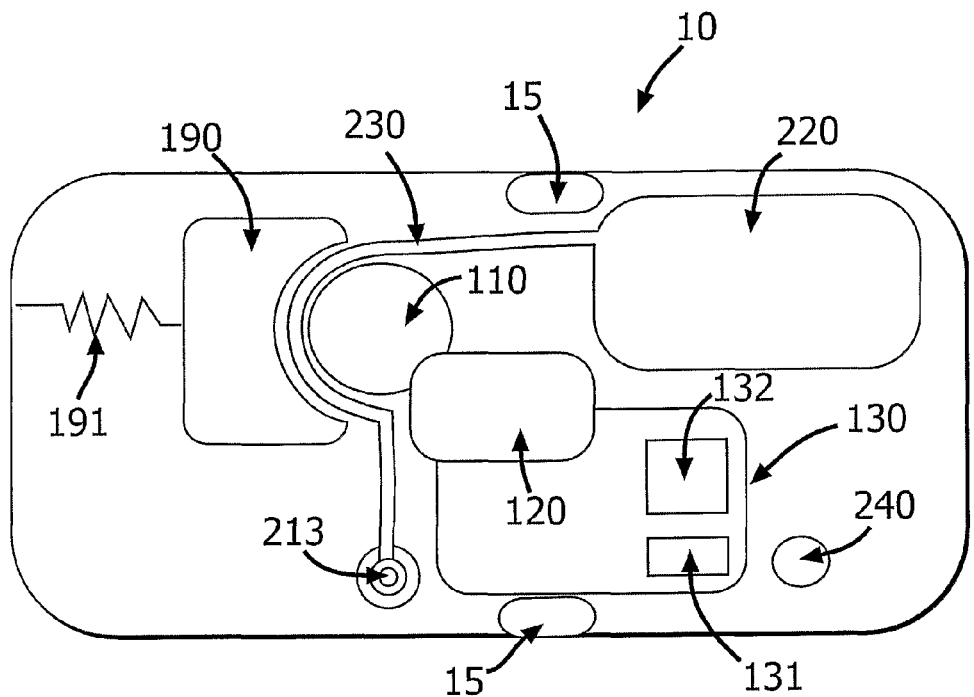
FIGS. 2a-b illustrate a single-part and two-part dispensing unit according to some embodiments.
Figure 2B:
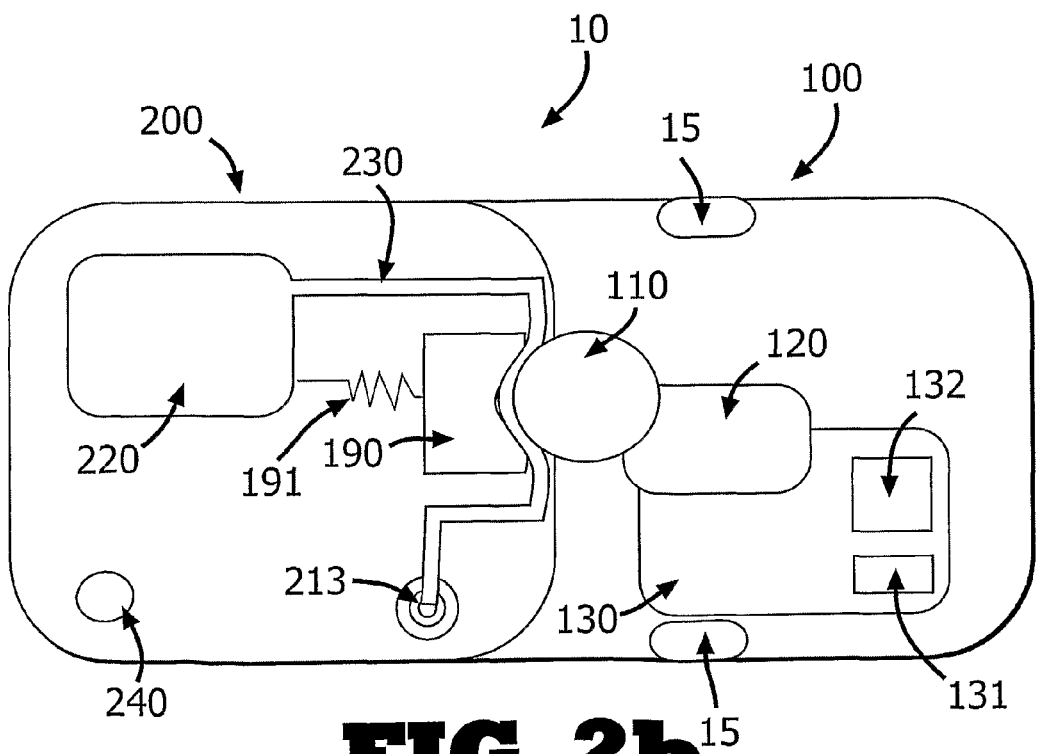

FIGS. 2a and 2b show embodiments of the dispensing unit (10) employing a peristaltic pumping mechanism for dispensing the fluid to the patient's body. FIG. 2a shows a single-part dispensing unit (10). The fluid is delivered from a reservoir (220) through a delivery tube (230) to an exit port (213). The peristaltic pumping mechanism includes a driving mechanism (120), a rotary wheel (110) having rollers (not shown in FIGS. 2a and 2b) and a stator (190) connected to a spring (191) that urges the stator (190) toward the rotary wheel (110). The delivery tube (230) passes between the stator (190) and the rollers, which are arranged such that rotation of the rotary wheel (110) and rollers allows the rollers to squeeze the delivery tube (230) against the stator (190). This results in periodic displacement of the fluid within the delivery tube (230) toward exit port (213). An example of a positive displacement pump is disclosed in co-owned, co-pending U.S. patent application Ser. No. 11/397,115 to Yodfat et al., filed Apr. 3, 2006, and entitled "Systems and Methods for Sustained Medical Infusion and Devices Related Thereto," the disclosure of which is incorporated herein by reference in its entirety. A driving mechanism (120) for rotating the rotary wheel (110) may include but is not limited to a gear and a motor. The motor may be without limitation a DC motor or an SMA actuator, which can be used for rotating the rotary wheel (110), where the rotary wheel (110) can be separate from the driving mechanism (120). The driving mechanism (120) can be controlled by electronic components (130), which include a processor (131) and a transceiver (132). An appropriate energy supply (240) can also be provided, which may include one or more batteries. Infusion programming can be carried out by a remote control unit (40) (not shown in FIGS. 2a and 2b) or by manual buttons (15), which can be provided on the dispensing unit (10). In some embodiments, the driving mechanism (120) may include a motor and at least one gear. In some embodiments, the peristaltic pumping mechanism includes a rotary wheel (110), a delivery tube (230), and a stator (190).

FIG. 2b shows an exemplary two-part dispensing unit (10). The reusable part (100) includes a peristaltic pumping mechanism comprising a driving mechanism (120), a rotary wheel (110), rollers (not shown), and a stator (190) connected to a spring (191). The reusable part (100) also includes electronic components (130) and driving mechanism (120), which includes gears and a motor. The disposable part (200) includes a reservoir (220), a delivery tube (230), an energy supply (240), an exit port (213), and a stator (190) connected to a spring (191).

Figure 3:
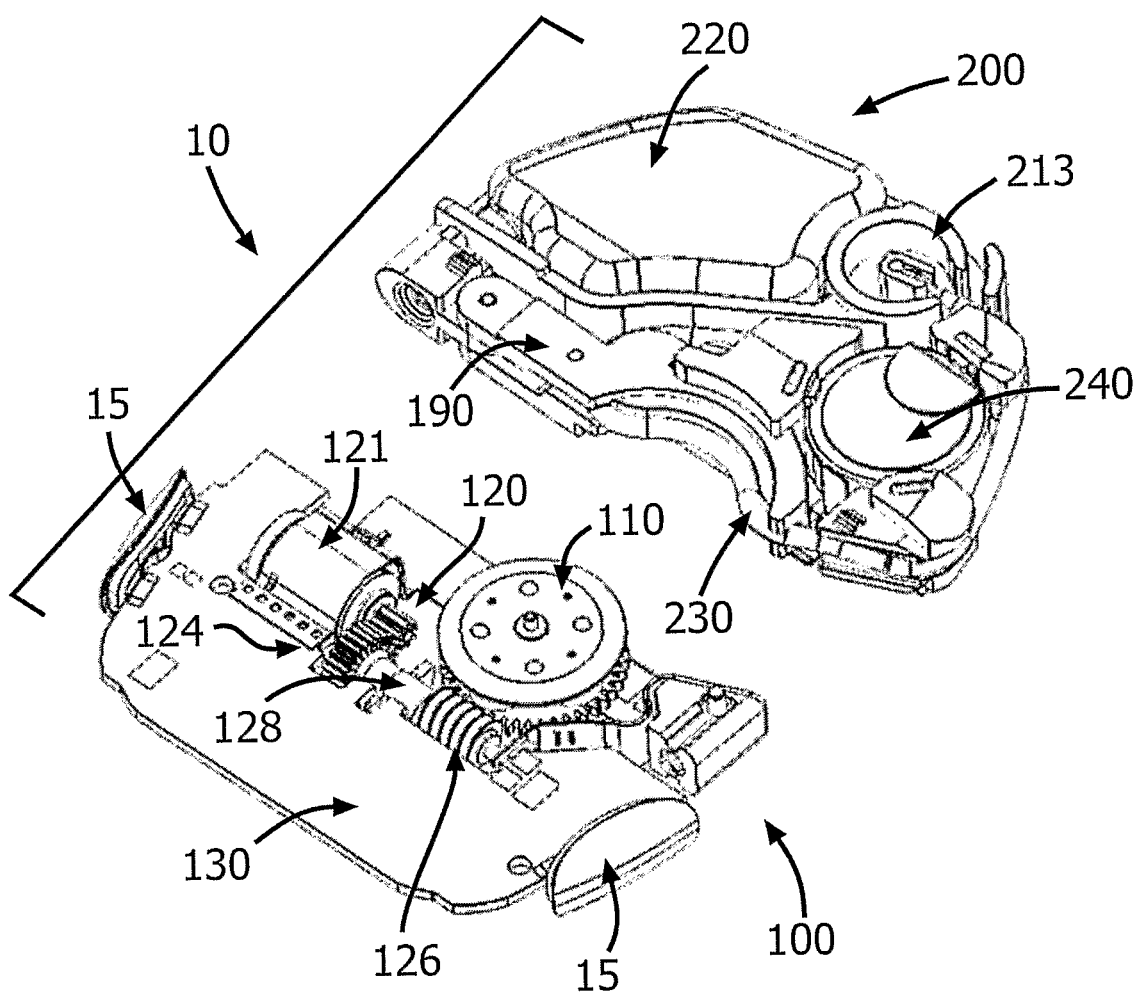
FIG. 3 illustrates main components of a two-part dispensing unit employing a peristaltic pumping mechanism according to some embodiments.
Figure 4:
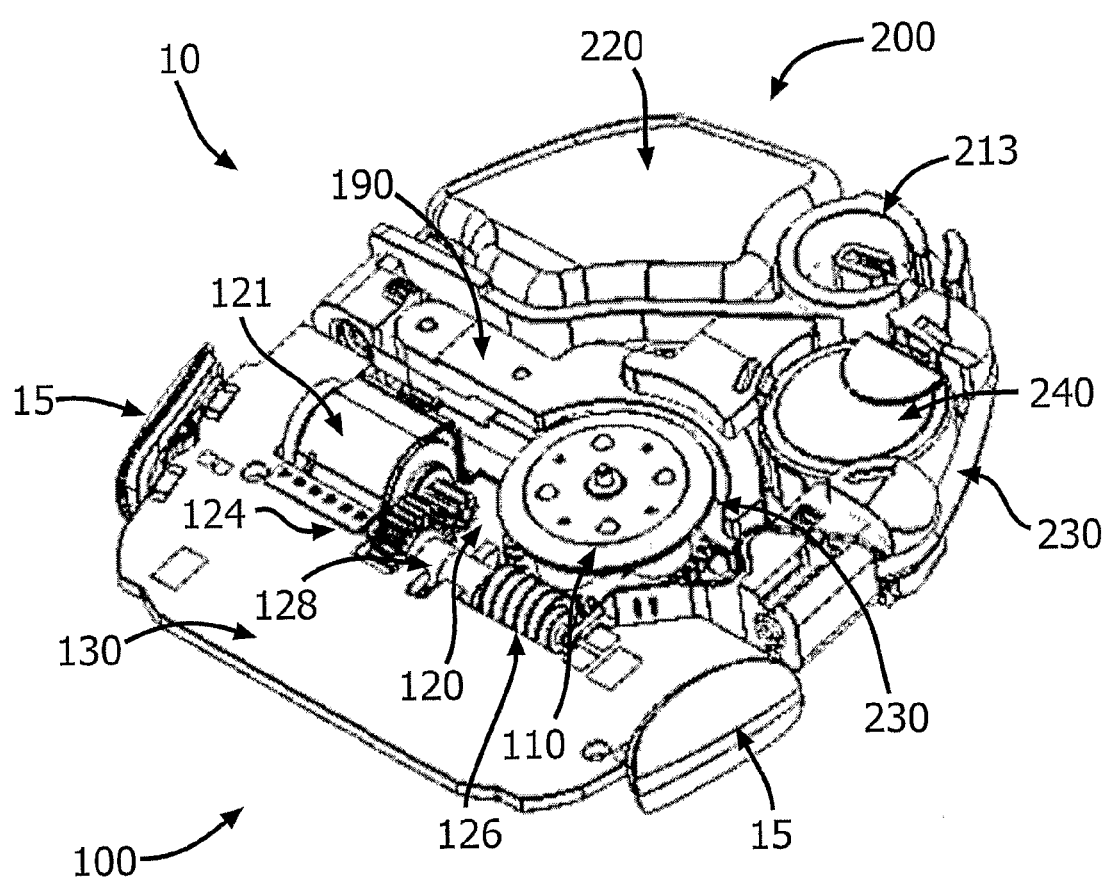
FIG. 4 illustrates a paired two-part dispensing unit employing a peristaltic pumping mechanism according to some embodiments.
Figure 5A:
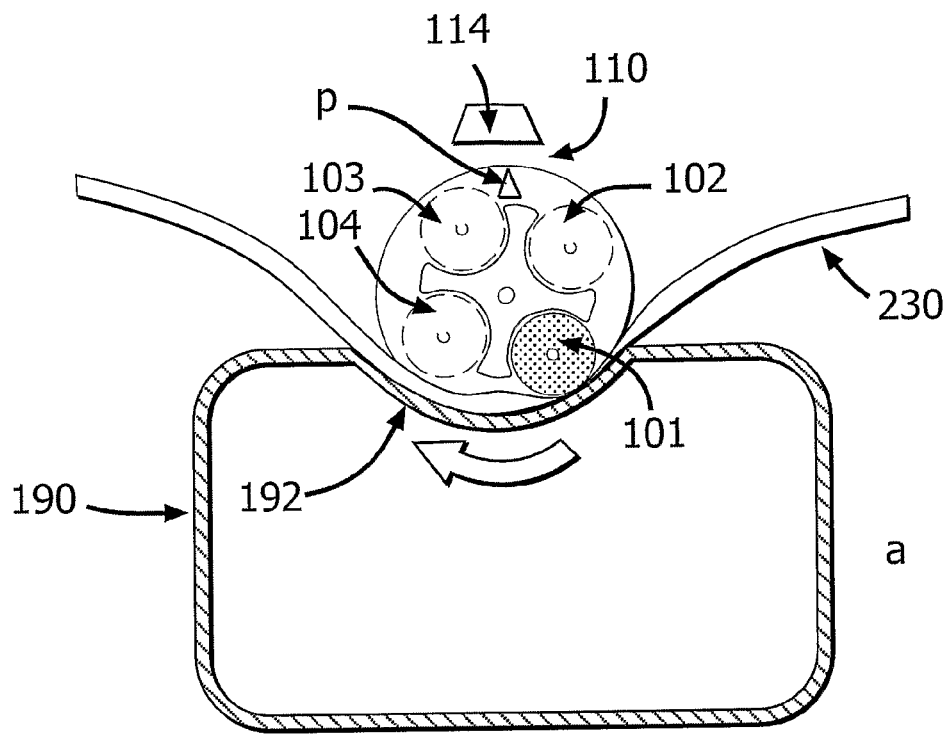
FIGS. 5a-h illustrate positions of rollers during phases of a rotary wheel period and the corresponding volumes of fluid delivered according to some embodiments.
Figure 5B:
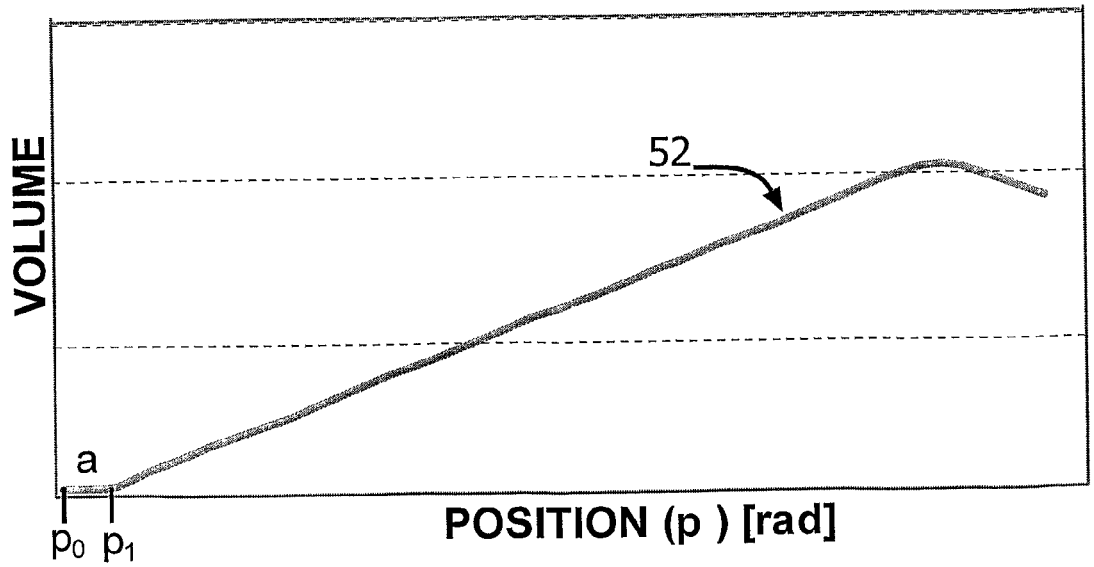
Figure 5C:
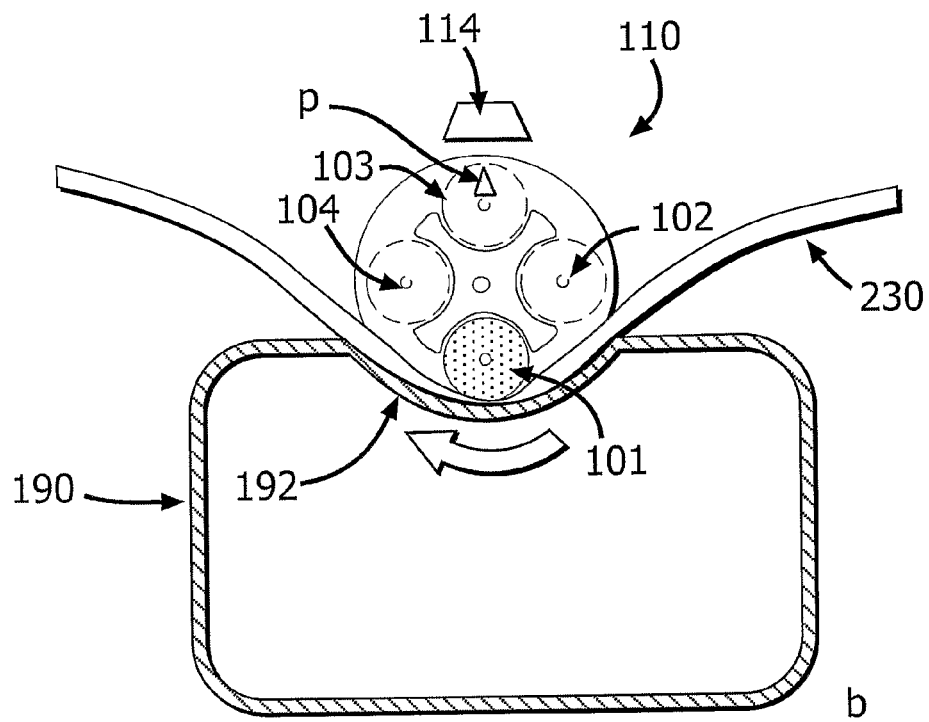
Figure 5D:
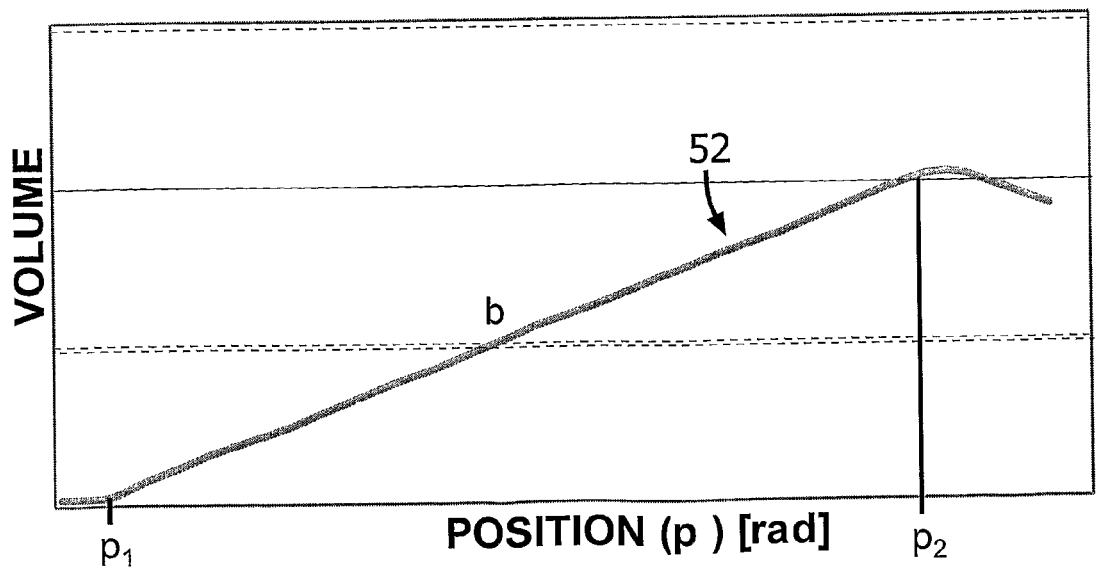
Figure 5E:
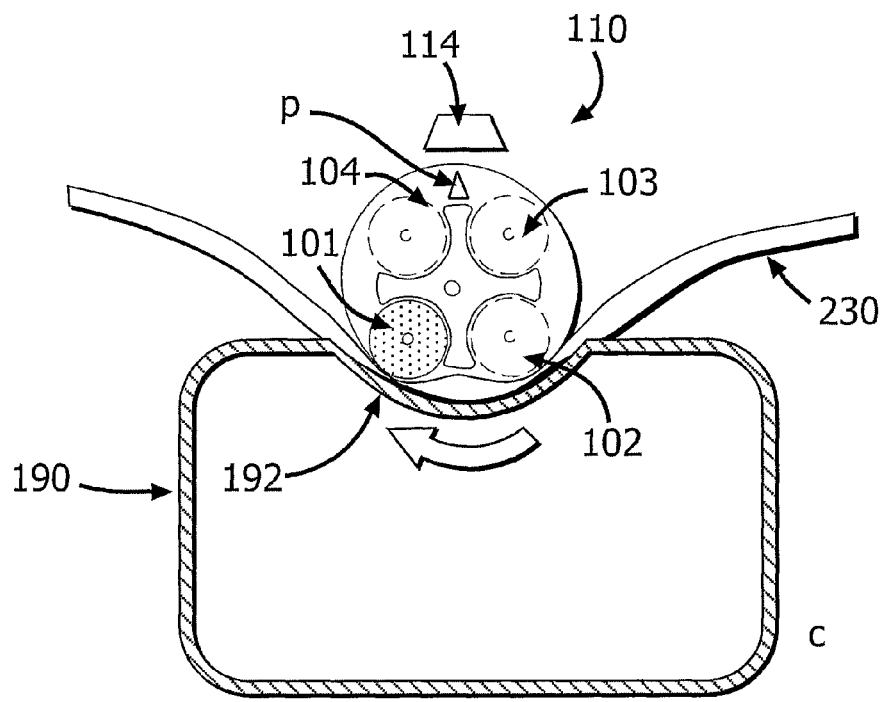
Figure 5F:
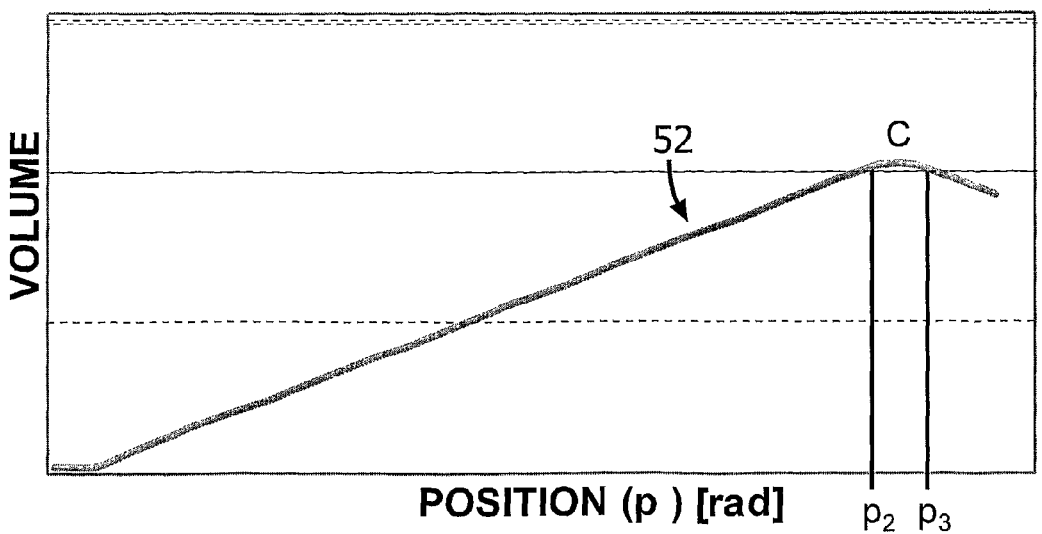
Figure 5G:
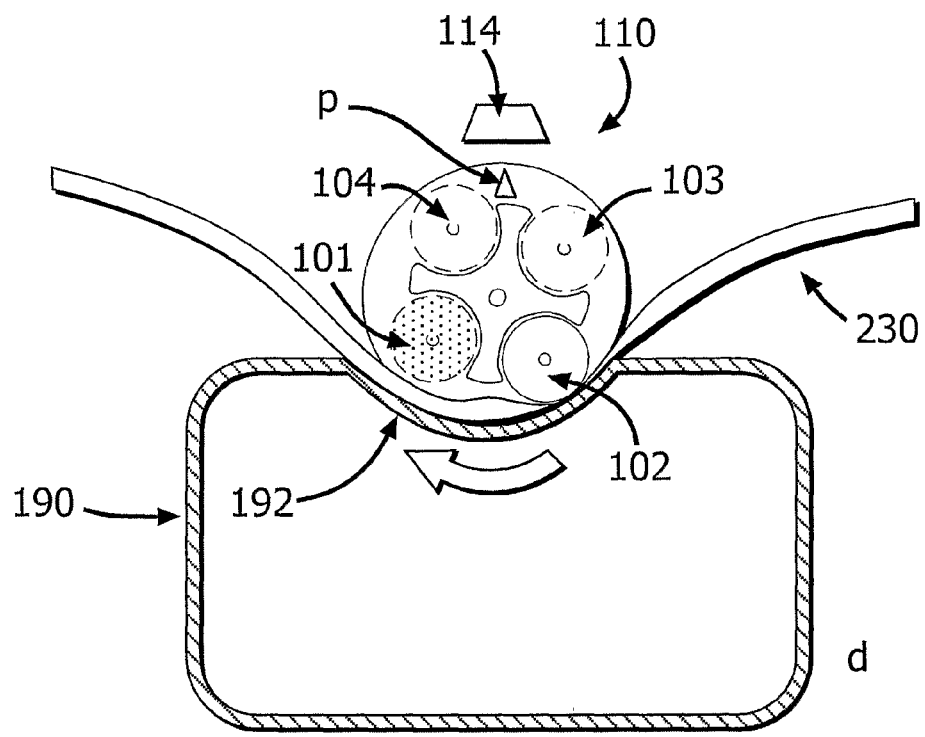
Figure 5H:
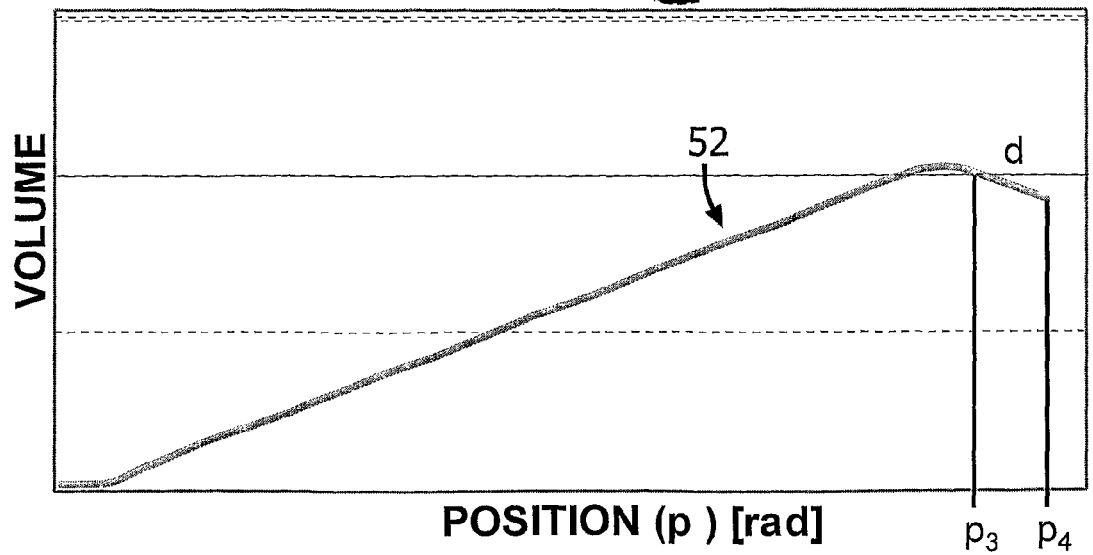

FIGS. 3 and 4 show an example of the two-part dispensing unit (10) before (FIG. 3) and after (FIG. 4) the reusable part (100) and the disposable part (200) are connected. The reusable part (100) includes a peristaltic pumping mechanism having rotary wheel (110), driving mechanism (120) with motor (121), a worm gear (126), a shaft (128), gears (124), and electronics (130). The disposable part (200) includes a reservoir (220), a delivery tube (230), an energy supply (240), an exit port (213) and a stator (190) connected to a spring (191).

FIGS. 5a-h show examples of rotation cycles of the rotary wheel (110) with four rollers (101, 102, 103, 104) and plots (52) depicting the amount of fluid delivered. The term "rotation" refers to any full or partial (e.g., ½ revolution or ¼ revolution) rotation of the rotary wheel (110). The rotary wheel (110) relative position ("p") is monitored by a sensor (114). A single roller's movement along the arched depression (192) of stator (190) can be divided into four consecutive phases, "a," "b," "c," and "d" shown in FIGS. 5a-h. Phases "a," "b," "c," and "d" are plotted in FIGS. 5a, 5c, 5e and 5g, respectively. That portion of the stator (190) corresponding to the roller's phases or period are bounded by points "$p_0$" to "$p_4$". The roller phases may also be characterized by the amount of fluid delivered based on changes in the roller's position in the rotary wheel (110). The correlations between the amount of fluid delivered and the change in position of the rotary wheel may be referred to as the flow characteristics of the fluid. The "flow characteristic" describes the relation between the positions of the rotary wheel and the amount of fluid delivered as a result of the rotary wheel's movement through such positions. The plots (52) in FIGS. 5b, 5d, 5f, and 5h depict this relationship. And columns 3 and 4 in Table 1 below show how the amount of fluid delivered (i.e., the flow) is characterized by, or correlates to, the relative position (p) of the rotary wheel, where the volume delivered is represented as V(p).

TABLE 1

Volume of Fluid Delivered Based on the Roller's Position

| Roller phase | Description | Phase's bounds | Volume Delivered (V(p)) |
|---|---|---|---|
| a | Roller (101) squeezes delivery tube (230) after roller (104) disengages from delivery tube (230) | $p_0 \leq p < p_1$ | $k * (p^2 - p_0^2)$ |
| b | Roller (101) moves forward | $p_1 \leq p < p_2$ | $k' * (p - p_1)$ |
| c | Roller (102) and roller (101) squeeze delivery tube (230) | $p_2 \leq p < p_3$ | $k'' * (p - p_2)$ |
| d | Roller (101) disengages from delivery tube (230), which restores its rounded cross-sectional shape and allows a backflow | $p_3 \leq p < p_4$ | $k''' * (p - p_3)$ |

The coefficients (k, k', k'', k''') can be determined empirically or by calculation. For example, k' correlates to the inner diameter of the delivery tube (230), and k, k'' and k''' correlate to the roller and rotary wheel (110) dimensions, as do $p_i$, $p_2$, and $p_3$.

The engagement between each roller (101, 102, 103, 104) and the delivery tube (230) starts at "$p_0$" and ends at "$p_4$," and as noted above is referred to as the "roller period". As one cycle of the rotary wheel (110) is equal to $2\pi$, a roller's period is equal to $2\pi$ divided by the number of rollers within the rotary wheel (110). For example, the roller period for a single roller in a three-roller rotary wheel (110) is equal $2\pi/3$, thus, $p_0=0$ and $p_4=2\pi/3$.

The volume delivered, V(p), of the peristaltic, pumping mechanism during roller phase "b" is: $k'*(p-p_1)$, when the initial position of the rotary wheel (110) is equal to $p_1$. If the initial position, $p_i$, of the rotary wheel (110) is $p_0$, then fluid is also delivered during roller phase "a". Hence, $$V(p) = k*(p_1^2 - p_0^2) + k'*(p - p_1) \qquad (1)$$

V(p) during a full roller period of $p_0$ to $p_4$ is thus calculated by summing the volumes delivered during the four phases ("a" to "d") as follows:

$$V(p) = k*(p_1^2 - p_0^2) + k'*(p - p_1) + k''*(p_2 - p_3) + k'''*(p_4 - p_3) \qquad (2)$$

Table 2 provides sample values for parameters shown in Table 1. These values are provided here for illustrative purposes only and are not intended to limit the scope of the disclosure.

TABLE 2

Sample Parameter Values

| Roller phase | Lower phase bound [rad] | Upper phase bound [rad] | Coefficient k [μL/rad] | (V(p)) [μL] |
|---|---|---|---|---|
| a | $p_0 = 0$ | $p_1 = 0.1$ | k = 0.1 | $0.01 \cdot (p^2 - 0)$ |
| b | $p_1 = 0.1$ | $p_2 = 1.3$ | k' = 0.23 | $0.23 \cdot (p - 0.1)$ |
| c | $p_2 = 1.3$ | $p_3 = 1.4$ | k'' = 0 | $0 \cdot (p - 1.3)$ |
| d | $p_3 = 1.4$ | $p_4 = 1.57 (\pi/2)$ | k''' = -0.16 | $-0.16 \cdot (p - 1.4)$ |

V(p) during full roller period using values from Table 2 is:

$$V(p) = 0.1 \cdot (0.1^2 - 0) + 0.23 \cdot (1.3 - 0.1) + 0 \cdot (1.4 - 1.3) - 0.16 \cdot (1.57 - 1.4) = 0.25 \, [\mu L] \qquad (3)$$

In some embodiments, the rotary wheel (110) can be provided with three rollers. Thus, the period for each roller is $2\pi/3$. An example of the volume of fluid delivered according to the change of a roller's position and the bounds of each roller phase are shown in Table 3 below. The values illustrated in Table 3 are provided for illustrative purposes only and not intended to limit the scope of the disclosure. Referring to the example shown in Table 3, when a roller moves within phases "a" and "b", the therapeutic fluid is delivered from the dispensing unit into the patient's body. When a roller is within phase "c", a backflow occurs, i.e. the therapeutic fluid moves backwards into the dispensing unit, thus reducing the amount of fluid delivered to the patient's body. When a roller moves within phase "d", there is no flow, i.e. the roller presses the tube and blocks any fluid delivery, and thus may be used as a valve. Referring to the example shown in Table 2, during phases "a" and "b" fluid is delivered to the patient's body, backflow occurs during phase "d", and the tube is blocked during phase "c".

TABLE 3

Sample of Volume of Fluid Delivered

| Roller phase | Lower phase bound [rad] | Upper phase bound [rad] | Coefficient k [μL/rad] | (V(p)) [μL] |
|---|---|---|---|---|
| a | $p_0 = 0$ | $p_1 = 0.1$ | k = 0.2 | $k \cdot \sin(p - p_0)$ |
| b | $p_1 = 0.1$ | $p_2 = 1.9$ | k' = 0.2 | $k' \cdot (p - p_1)$ |
| c | $p_2 = 1.9$ | $p_3 = 2.0$ | k'' = 0.3 | $k'' \cdot (p_2 - p)$ |
| d | $p_3 = 2.0$ | $p_4 = 2.09 (2\pi/3)$ | k''' = 0 | $k''' \cdot (p - p_3)$ |

V(p) during a full roller period using values from Table 3 is:

$$V = 0.2 \cdot \sin(0.1 - 0) + 0.2 \cdot (1.9 - 0.1) + 0.3 \cdot (1.9 - 2) + 0 \cdot (2\pi/3 - 2) = 0.35 \, \mu L \qquad (4)$$

Figure 6:
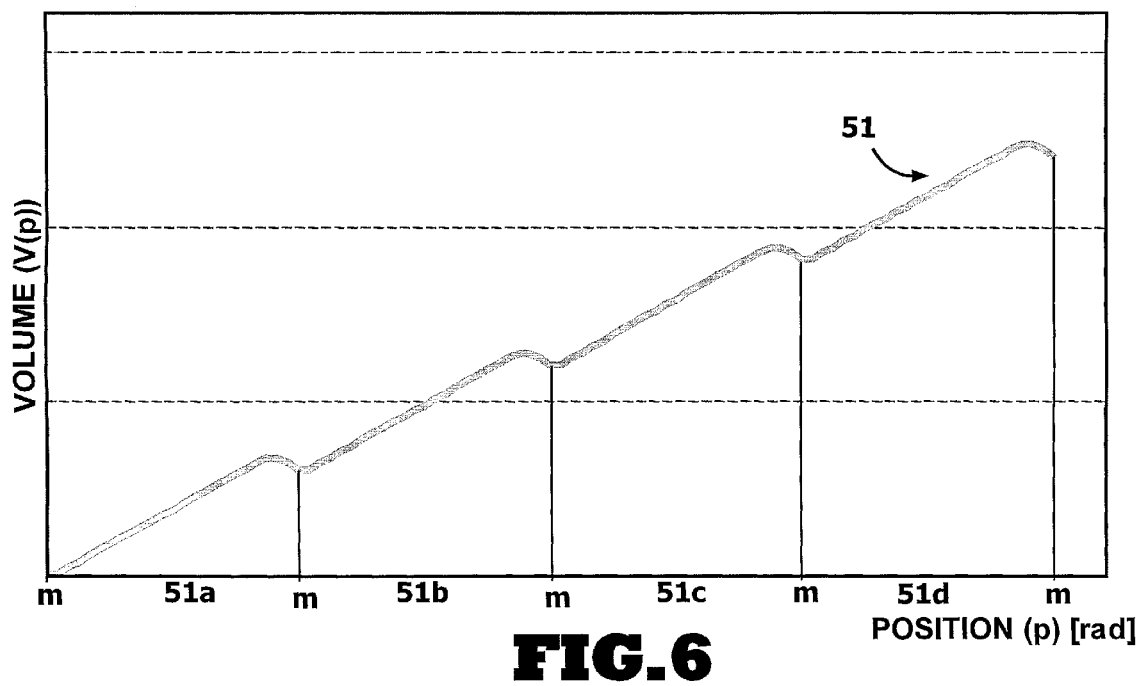
FIG. 6 illustrates volume dosages delivered by the peristaltic pumping mechanism during a single period of rotation of a rotary wheel provided with four rollers according to some embodiments.

FIG. 6 illustrates an exemplary plot (51) of volume delivered according to the change in the position of a rotary wheel (110) during one rotation of a rotary wheel (110) having four rollers. Each roller phase (51a, 51b, 51c, 51d) starts at a local minimum point ("m") and ends in the subsequent local minimum point. When a roller leaves the local minimum point, a backflow of fluid in the delivery tube (230) occurs. The volume delivered during one period of the rotary wheel (110) equals the number of the rollers multiplied by the volume delivered during a period of a single roller. For example, a rotary wheel (110) having four rollers delivers 1 μL (0.25*4=1) during one period because each roller's period delivers 0.25 μL (as shown in FIGS. 5a-h).

Figure 7A:
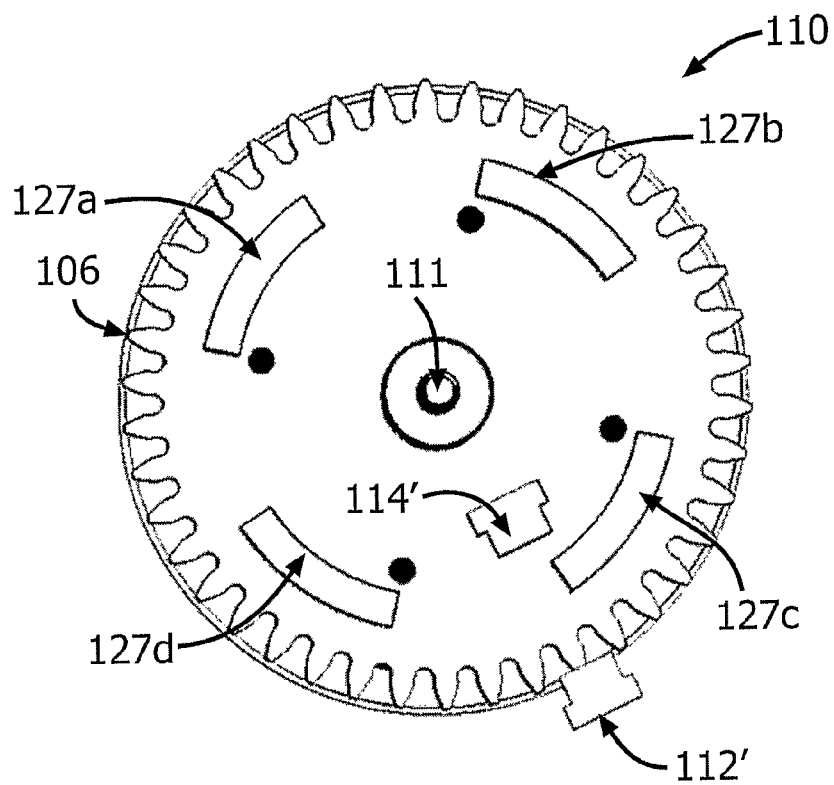
FIGS. 7a-b illustrate a sensor located on the rotary wheel according to some embodiments.
Figure 7B:
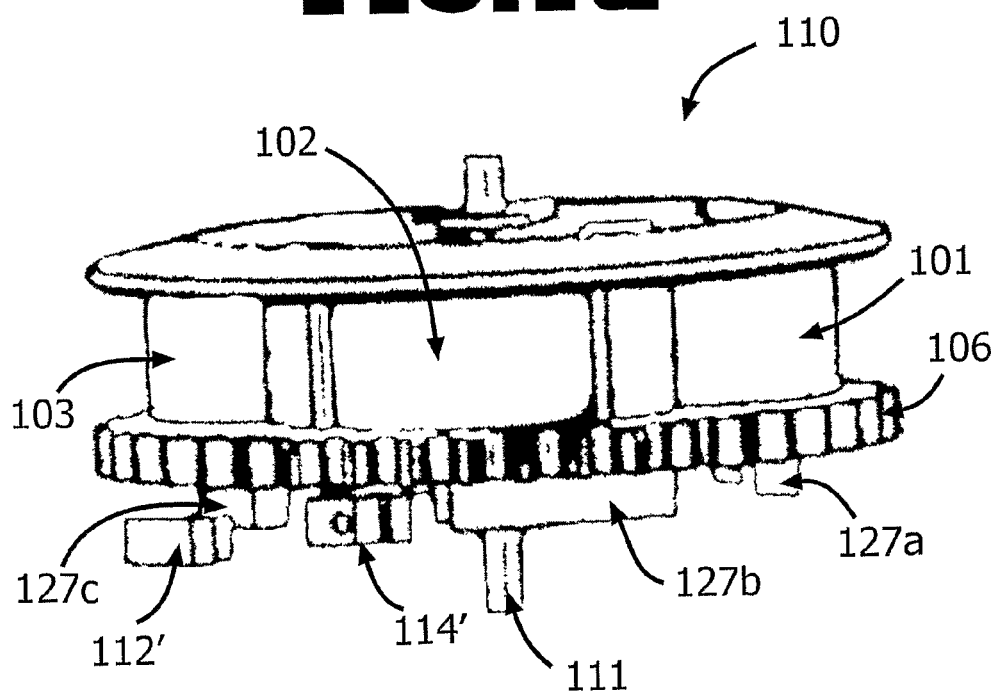

FIGS. 7a and 7b illustrate an embodiment of a sensor for monitoring a relative position (p) of the rotary wheel (110). The sensor may comprise a light-emitting source (112') (e.g., an LED) and a light detector (114') (e.g., a phototransistor), collectively referred to as a photointerruptor. The gear (106) of the rotary wheel (110) is provided with four equally spaced protrusions (127a, 127b, 127c, 127d) aligned with the four rollers (101, 102, 103, 104). The protrusions (127a, 127b, 127c, 127d) intermittently block the light emitted by the light-emitting source (112') because the light-emitting source (112') and the light detector (114') are located on opposite sides of the protrusions (127a, 127b, 127c, 127d). The photointerruptor detects when the protrusions (127a, 127b, 127c, 127d) block the light emitted by the light-emitting source (112') and generates "on-off" signals to be transmitted to a processor (not shown). The processor receives the "on-off" signals and interprets them to determine a relative position (p) of the rotary wheel (110) and, in turn, the amount of fluid delivered by the movement of the rotary wheel (110) based on the correlations between "p" and "V" noted above with respect to FIGS. 5a-h.

Figure 8A:
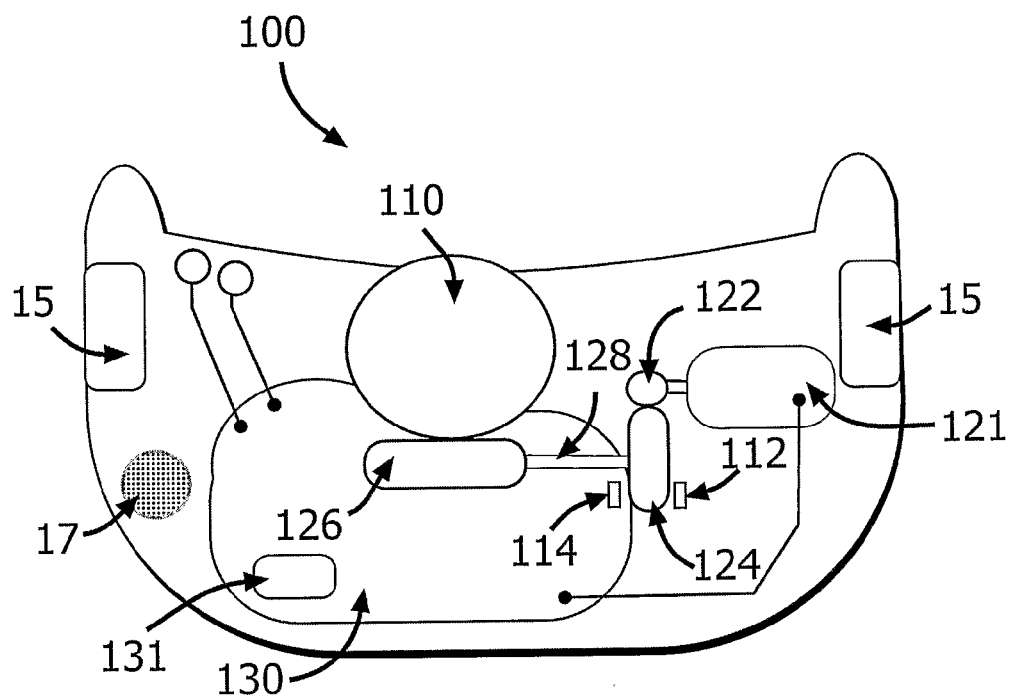
FIGS. 8a-b illustrate an encoder wheel fixed on a worm shaft and a photo-interrupter according to some embodiments.
Figure 8B:
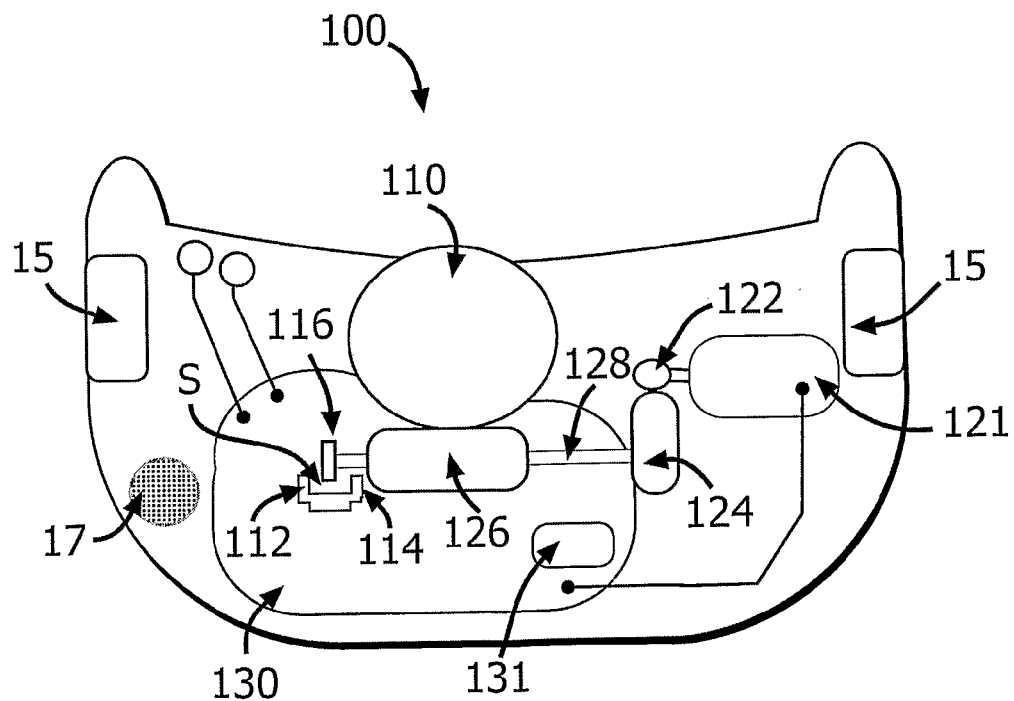

FIGS. 8a and 8b illustrate embodiments of the reusable part (100), which includes a rotary wheel (110), motor (121), pinion (122), secondary gear (124), worm gear (126), and shaft (128). FIG. 8*a* shows a photointerruptor (e.g., light-emitting source (112) and light detector (114)), which monitors rotation of the secondary gear (124). The relative position (p) of the rotary wheel (110) is derived from the known gear ratio between the rotary wheel (110) and the secondary gear (124). For example, if the gear ratio is 1:8, then during eight revolutions of the secondary gear (124), the rotary wheel (110) performs one revolution. FIG. 8*b* illustrates an embodiment where the photointerruptor monitors rotation of the shaft (128). "On-off" light signals are generated by the rotation of an encoder vane (116) when it passes a space "S" between the light-emitting source (112) and the light detector (114). The encoder vane (116) can be located at the end of the shaft (128), as shown in FIG. 8*b*, or at any other location along the shaft (128) (e.g., between secondary gear (124) and worm gear (126), as illustrated in FIG. 9).

Figure 9:
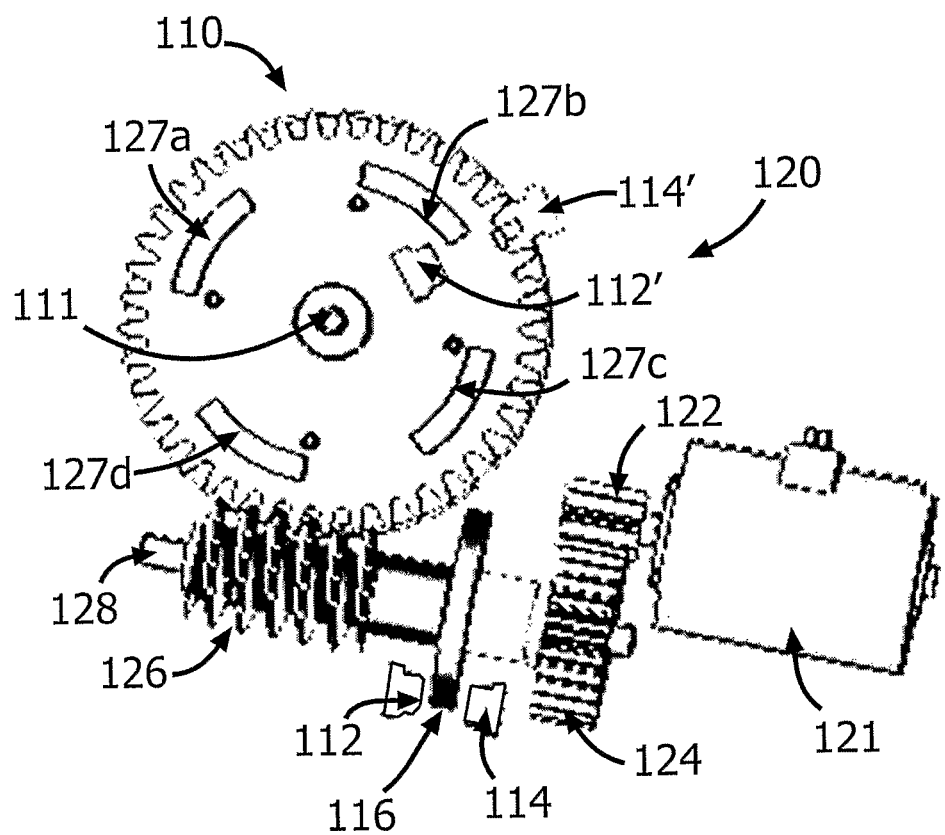
FIG. 9 illustrates two sensors for monitoring phases of a rotation period of a rotary wheel and a shaft.

FIG. 9 illustrates an embodiment that includes two sensors for monitoring rotation of the rotary wheel (110) and the shaft (128): (i) using a photointerruptor (light-emitting source (112') and light detector (114')), or (ii) using an encoder vane (116) with a photointerruptor (light-emitting source (112) and light detector (114)). The two sensors can be synchronized as follows:

provide overlapping signals for higher reliability.

provide consecutive signals for higher resolution of a rotating component's relative position (p).

Figure 10:
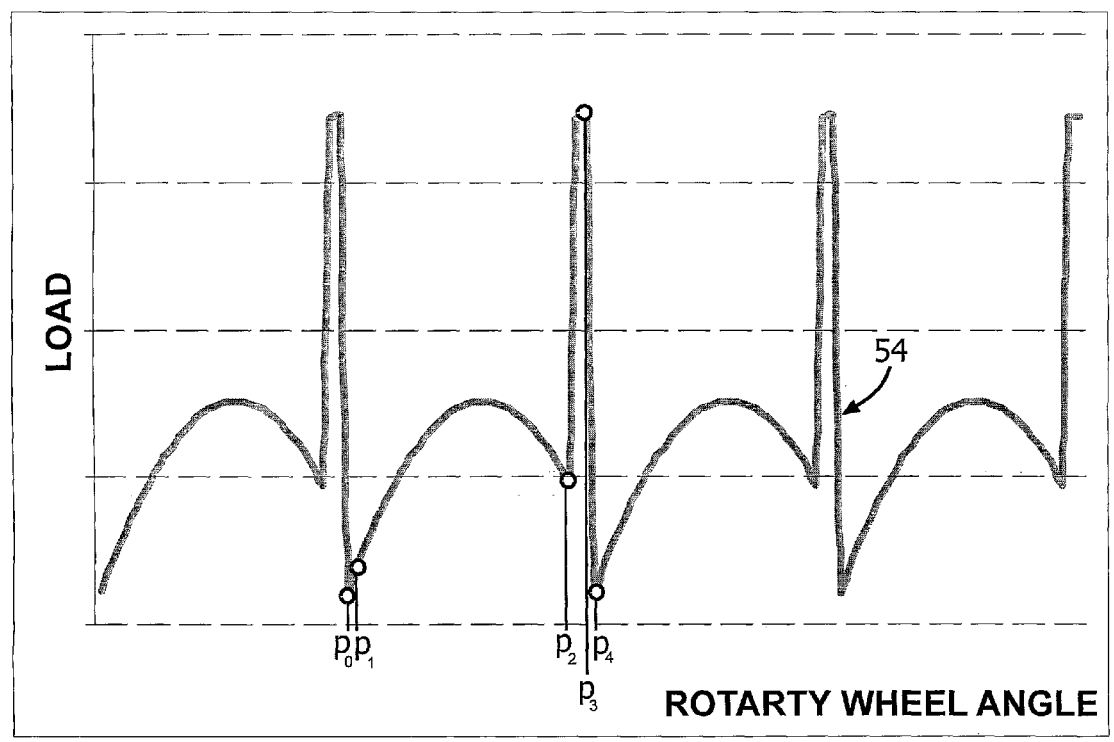
FIG. 10 illustrates dependence of the load on the stator's spring as a function of rotary wheel cycle phase.

FIG. 10 shows a plot (54) depicting spring load as a function of the phase of rotation of a rotary wheel (110) having four rollers. The points marked "$p_0$," "$p_1$," "$p_2$," "$p_3$," and "$p_4$" indicate the bounds of each roller's phase, as shown in FIGS. 5*a-h*. The changes in the spring load can be correlated with roller phases and consequently with the volume delivered, which can be adjusted by the processor (not shown).

Figure 11:
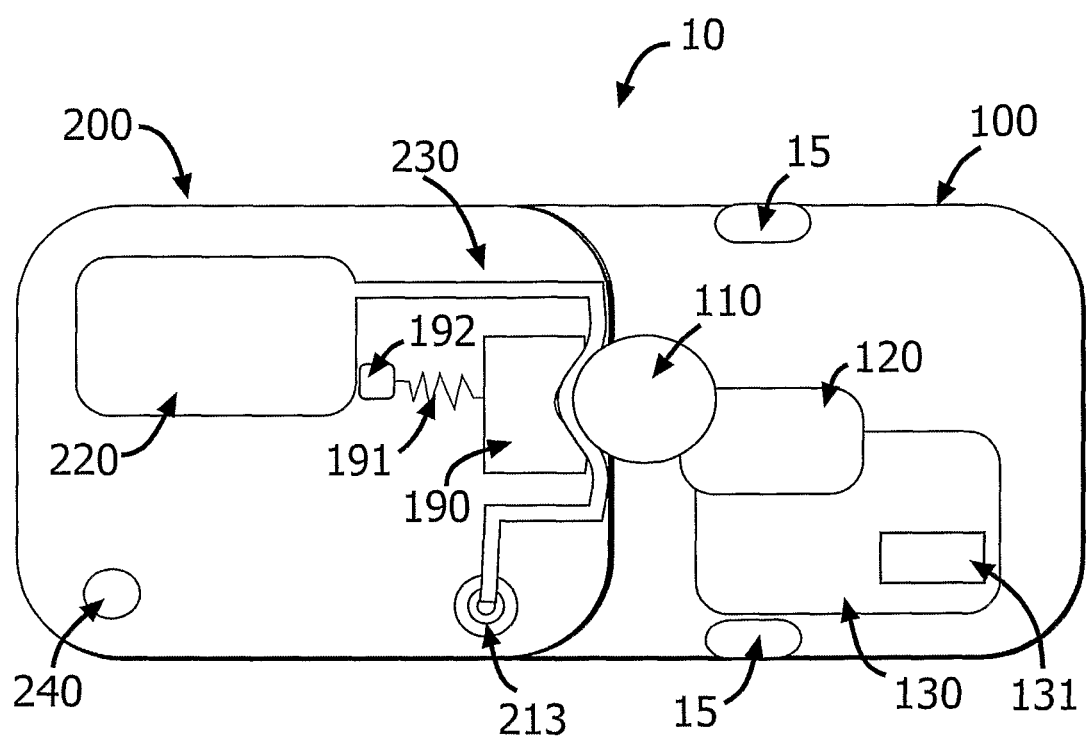
FIG. 11 illustrates a load cell attached to the stator's spring.

FIG. 11 illustrates an embodiment of the dispensing unit (10) having a reusable part (100) and a disposable part (200). The disposable part (200) includes an alternate monitoring mechanism for determining the amount of fluid delivered. The mechanism includes a sensor having a load cell (192) coupled to a spring (191), which in turn is coupled to the stator (190). As the rotary wheel's (110) rollers rotate and the stator (190) is pushed toward the rotary wheel (110), thus squeezing the delivery tube (230), the tension in spring (191) changes. Such change in the tension is detected by the load cell (192). The load cell (192) is configured to generate a signal indicative of the change in tension of the spring (191) and transmit the signal to the processor (131), which interprets the signal to determine the amount of fluid being delivered. One of ordinary skill in the art will appreciate that various ways of monitoring the amount of fluid being delivered using the rotary wheel (110) can be implemented in addition to the specific embodiments described herein.

Figure 12:
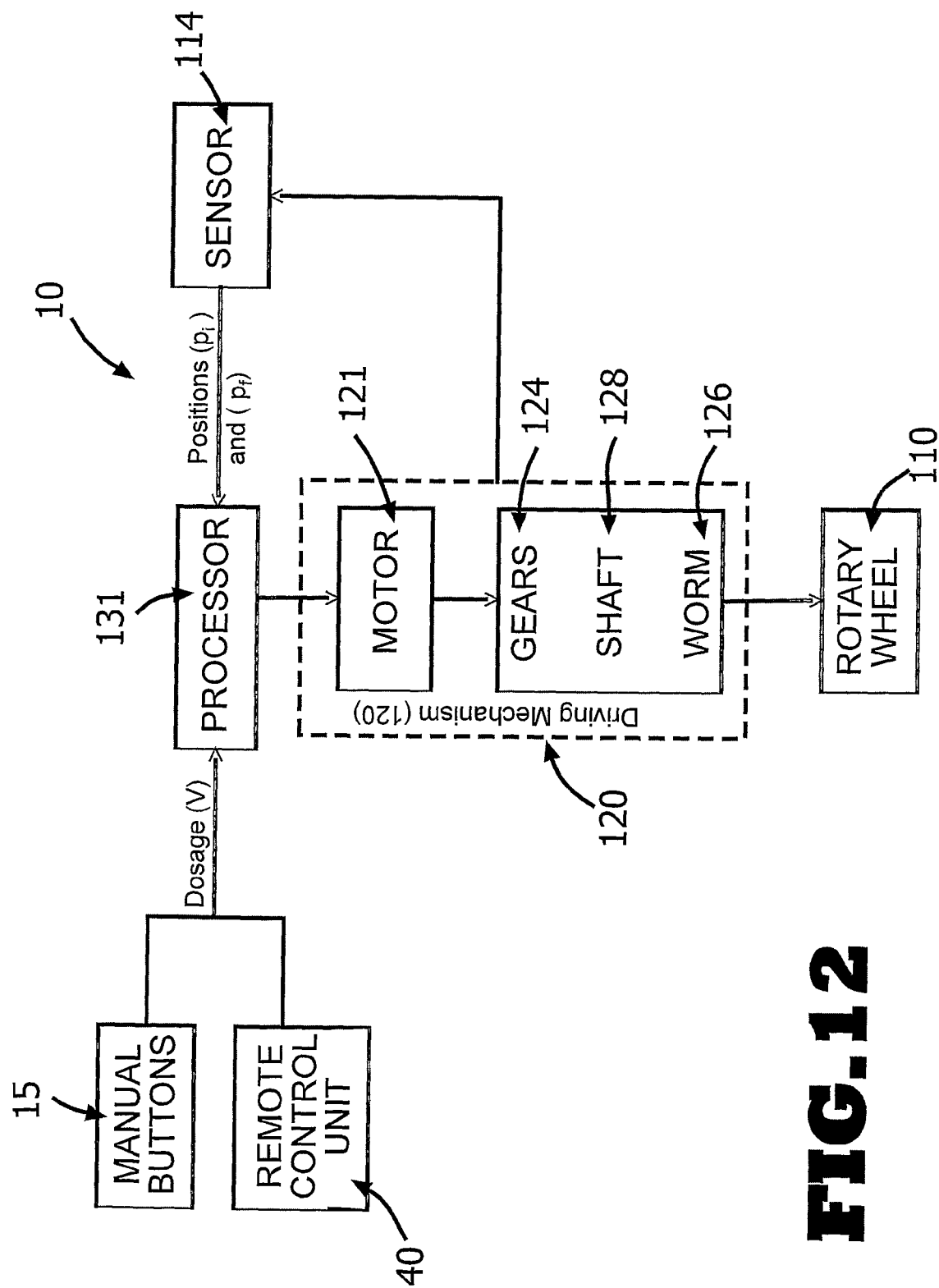
FIG. 12 illustrates a block diagram of closed-loop feedback for controlling the flow delivery.

FIG. 12 is an exemplary flow chart of the process for monitoring and controlling the flow of fluid delivered by a dispensing unit (10). The volume delivered (also referred to in FIG. 12 as "dosage" and designated as "V") is set by telemetry means, including but not limited to, a remote control unit (40) or manually-actuatable buttons (15). The setting can be automatically set or preprogrammed. The desired dosage can be obtained directly (e.g., as the amount of fluid to be delivered) by deriving it from other data, such as analyte (e.g., glucose) level in the patient's body or any other data. Processor (131) activates the motor (121) in the driving mechanism (120) based on the desired dosage. During rotation of the driving mechanism (120), the sensor (114) monitors the relative position (designated as "$p_i$" and "$p_f$") of the rotary wheel (110). The sensor (114) generates signals associated with the instant angular position of the rotary wheel (110) and transmits them to the processor (131), which determines the relative position (p) of the rotary wheel (110) and, in turn, the amount of fluid delivered by the movement of the rotary wheel (110) based on the correlations between "p" and "V", as shown for example in FIGS. 5*a-h*. The processor (131) may then adjust the motor (121) operation to deliver a dosage according to a dosage ("V") that has been already delivered.

Figure 13A:
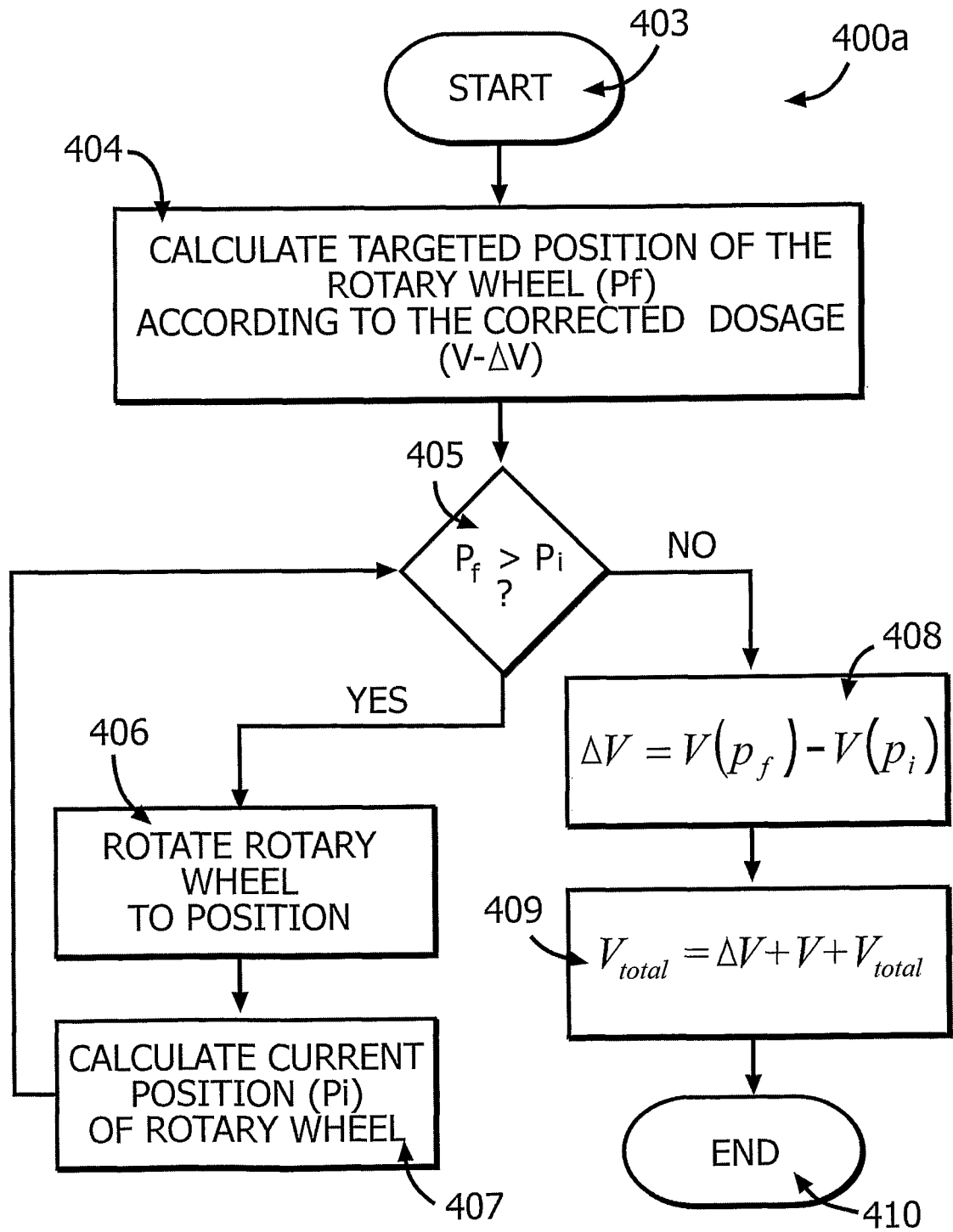
FIGS. 13a-c illustrate flow charts of the volume of fluid delivered adjusted according to the sensor inputs.
Figure 13B:
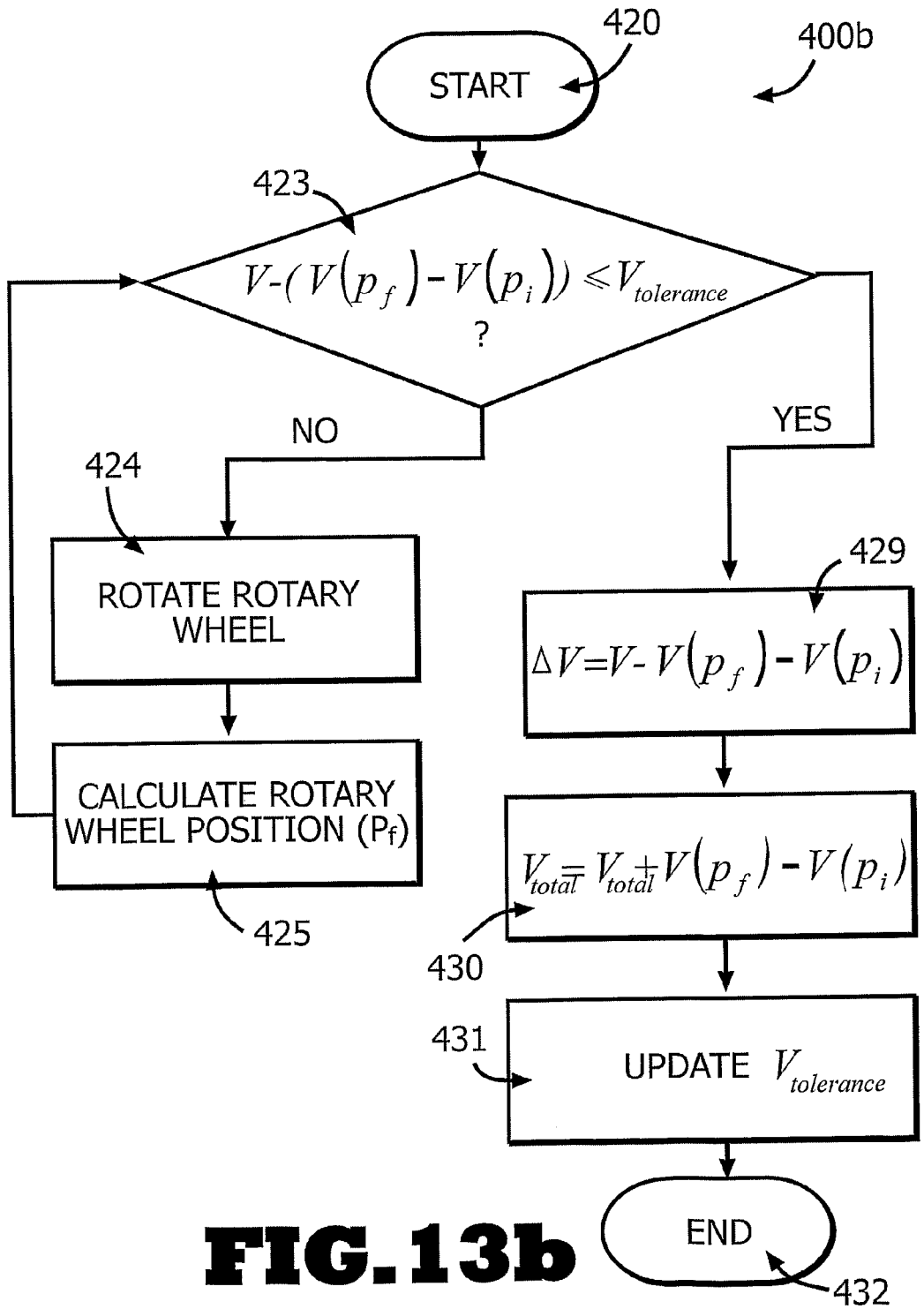
Figure 13C:
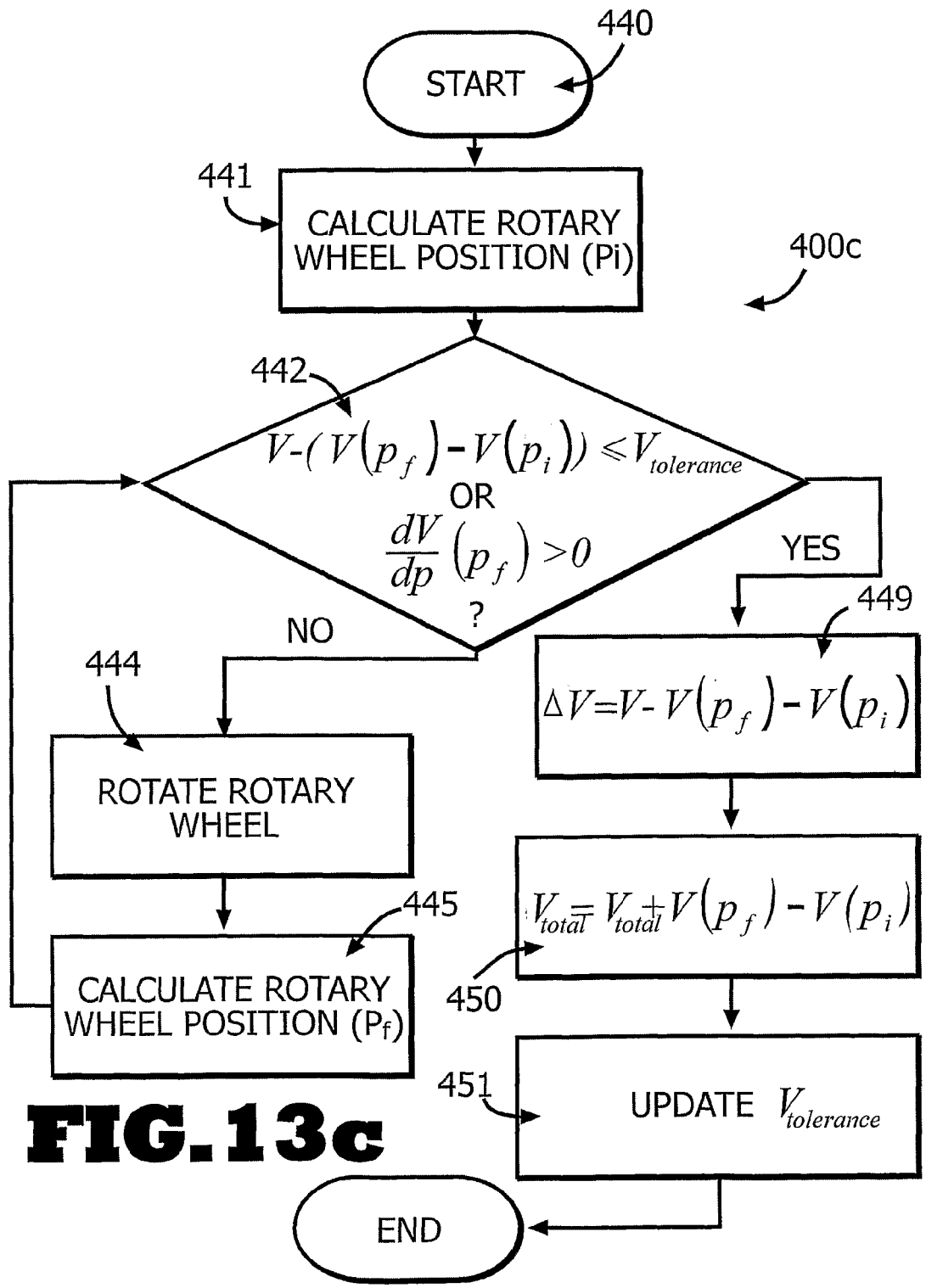

FIGS. 13*a-c* are exemplary flow charts depicting methods for delivery processing and correction of the therapeutic fluid flow rate that include calculation and correction of the therapeutic fluid flow rate. While the examples generally refer to a peristaltic pumping mechanism, the method may be implemented in a dispensing unit having other pumping mechanisms, including without limitation, a plunger or syringe pumping mechanism, flexible liner pumps or other types of positive displacement pumps. FIG. 13*a* shows an embodiment of a fluid delivery process (400*a*) where a preliminary determination of the rotary wheel targeted position ("$p_f$") is carried out before delivering the dosage. The targeted position, $p_f$, is calculated at Step 404 according to (i) the volume delivered, V(p), (ii) inaccuracies of prior fluid deliveries (designated as "ΔV"), and (iii) the current position of the rotary wheel (designated as "$p_i$") (shown in Step 407). In Step 405, if $p_f$ is greater than $p_i$, then fluid has not yet been delivered. Thus, fluid delivery is initiated in Step 406 by rotating the rotary wheel. In Step 407, the current position, $p_i$, is calculated. In returning to Step 405, if $p_f$ is no longer greater than $p_i$, the dosage has been delivered. At Step 408, ΔV is calculated as:

$$\Delta V = V(p_f) - V(p_i) \quad (5)$$

The total volume delivered by the pump (designated as "$V_{total}$") is updated at Step 409 as:

$$V_{total} = \Delta V + V + V_{total} \quad (6)$$

The process is terminated at Step 410.

FIG. 13*b* illustrates an embodiment of a fluid delivery process (400*b*) where tolerance level, "$V_{Tolerance}$," which provides a limit of deviation from a dosage V, is calculated during the rotation of the rotary wheel. "$V_{Tolerance}$" can be a fixed value or a variable according to various parameters. For example, $V_{Tolerance}$ may correlate to ΔV. The volume delivered during the current processing ($V(p_f) - V(p_i)$) is compared to V at Step 423. If $V - (V(p_f) - V(p_i)) \leq V_{Tolerance}$, the deviation from dosage V is within the tolerance level and processing is terminated after ΔV, $V_{total}$ and $V_{Tolerance}$ are updated at Steps 429, 430 and 431, respectively. If this is not the case, the pumping mechanism delivers fluid at Step 424 and the new position ($p_f$) of the rotary wheel (110) is measured at Step 425, in order to evaluate the amount of delivered fluid. Processing then returns to Step 423.

FIG. 13*c* illustrates an embodiment of a fluid delivery process (400*c*) where rotary wheel (110) is stopped only if the fluid is flowing from the dispensing unit (10) to the patient. Thus, the durations of the backflow and no flow, as well as the pulsations, are reduced. The direction of the flow can be determined by the derivative $$\left(\frac{dV}{dp}(p_f)\right)$$

of the volume delivered function, V(p), based on a roller's position:

When the fluid is delivered to the patient $$\frac{dV}{dp}(p_f) > 0.$$

When there is no flow $$\frac{dV}{dp}(p_f) = 0.$$

On backflow $$\frac{dV}{dp}(p_f) < 0.$$

Figure 14A:
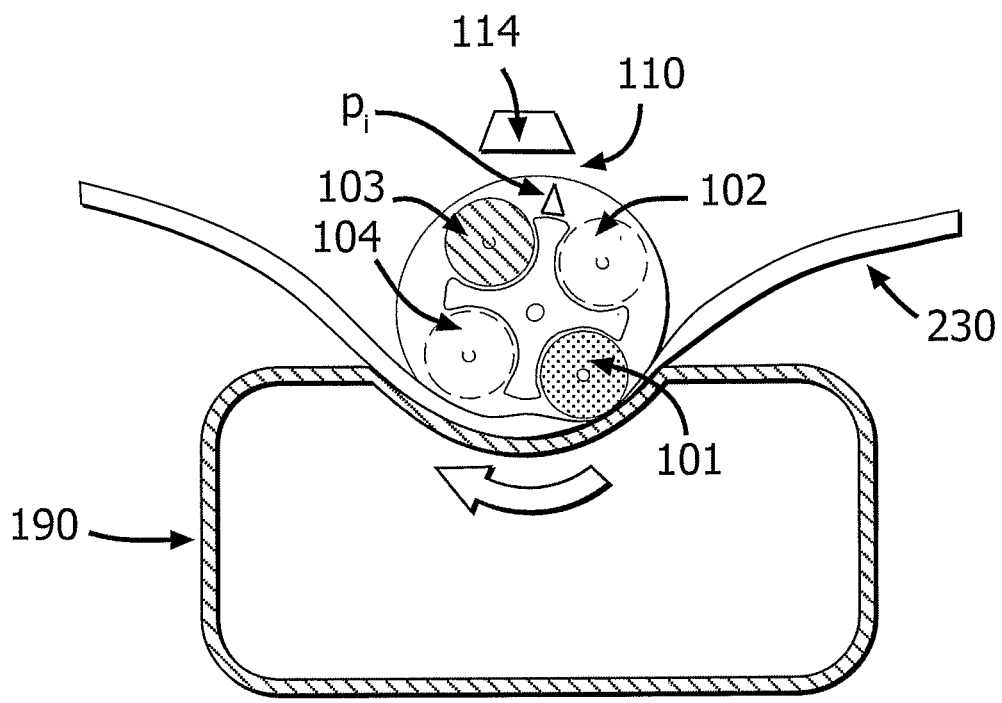
FIGS. 14a-o illustrate examples of the volume, of fluid delivered in each phase of the rotation period of the rotary wheel adjusted as shown in FIGS. 13a-c.
Figure 14B:
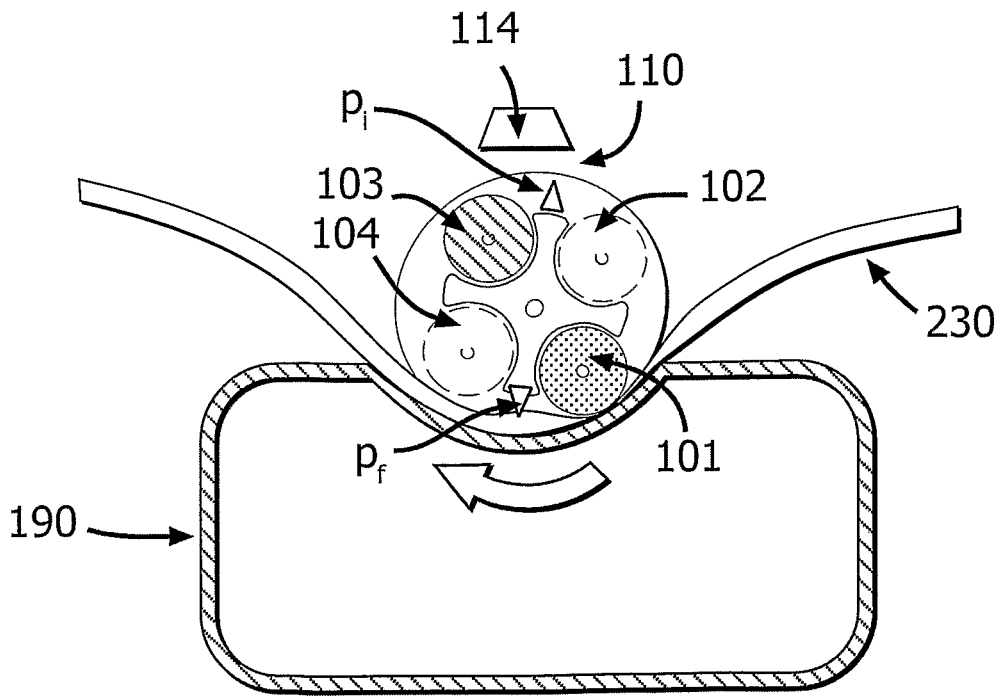
Figure 14C:
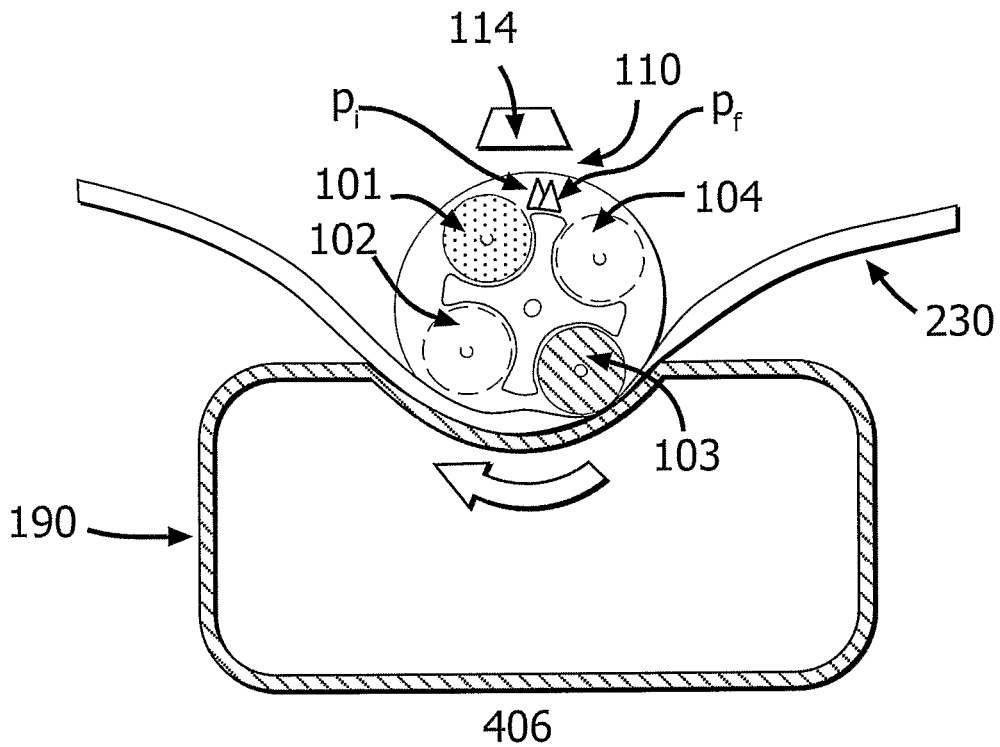
Figure 14D:
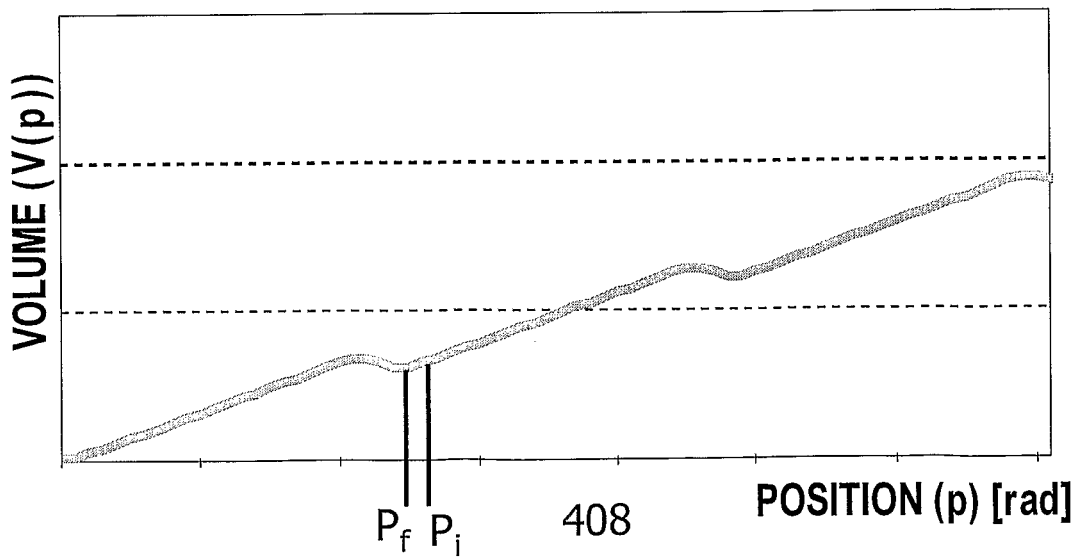
Figure 14E:
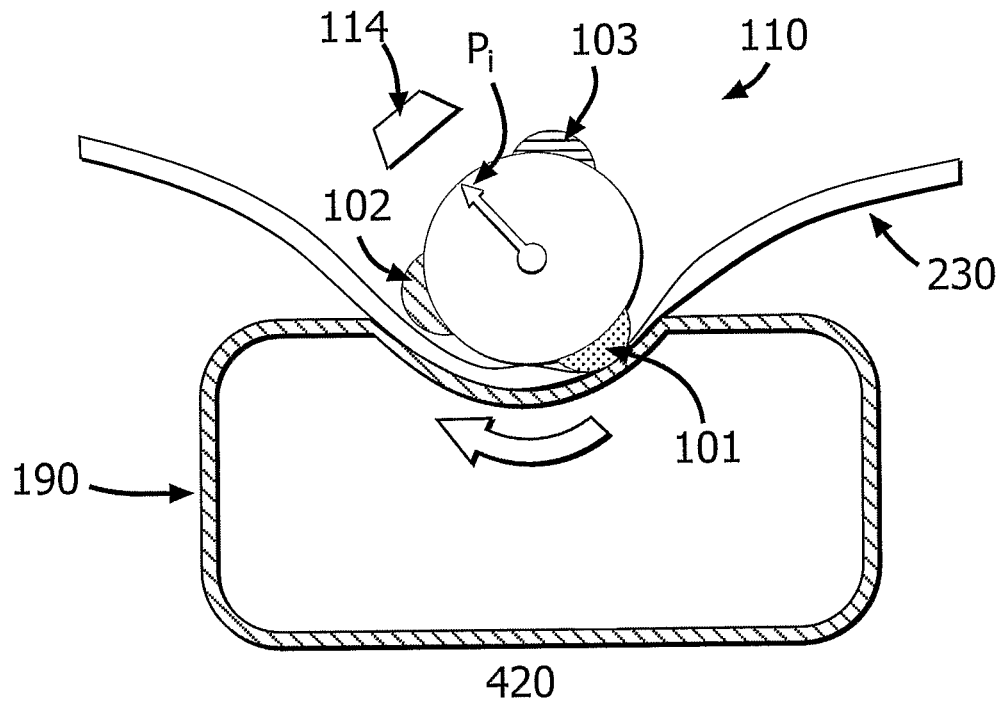
Figure 14F:
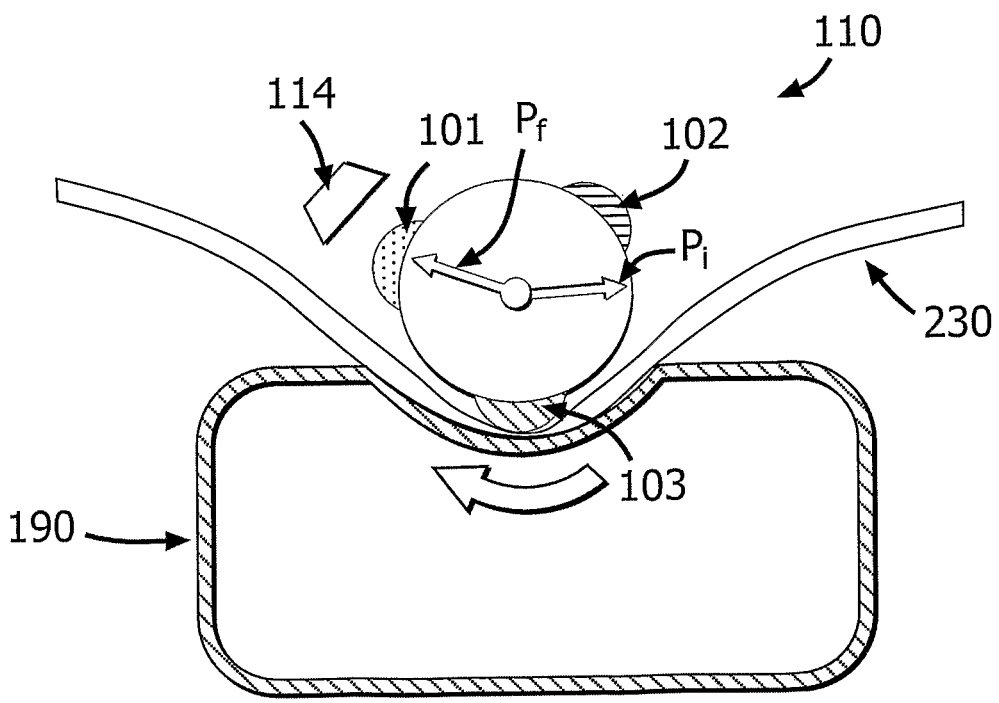
Figure 14G:
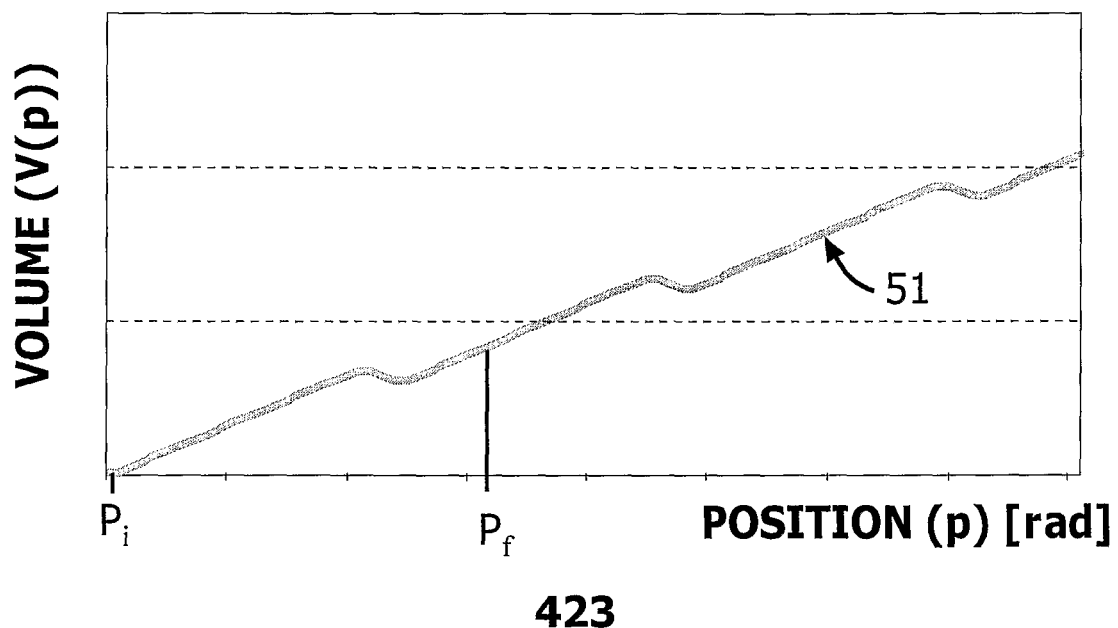
Figure 14H:
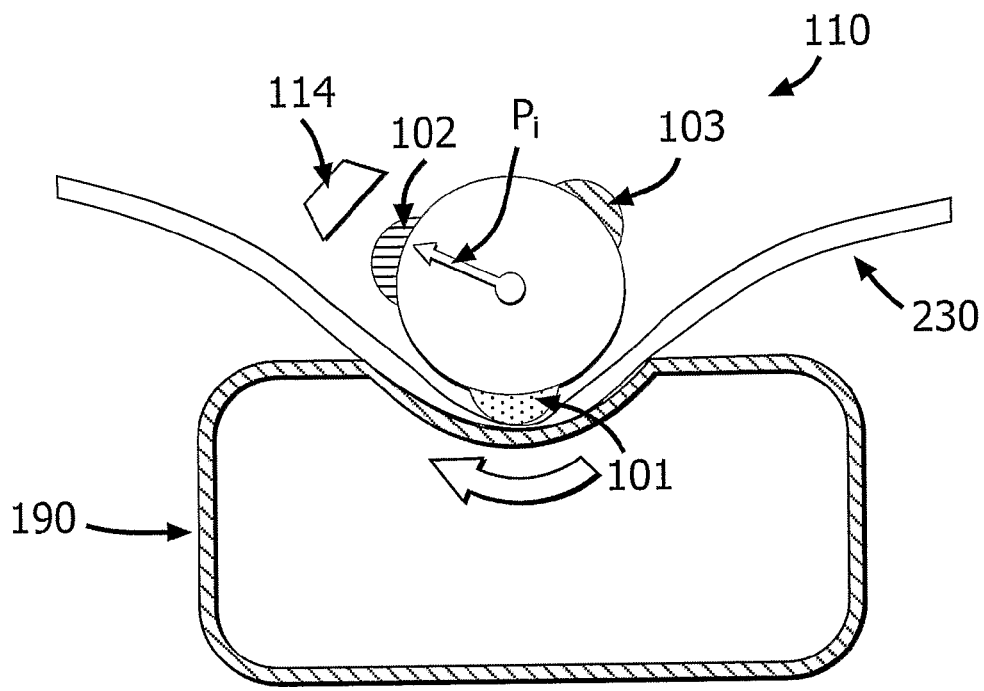
Figure 14I:
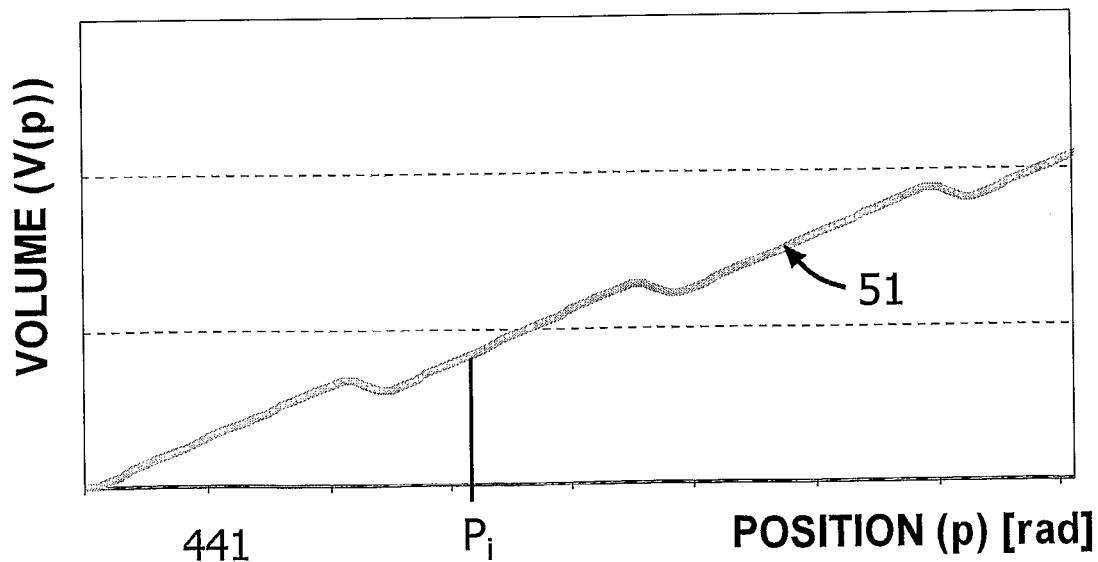
Figure 14J:
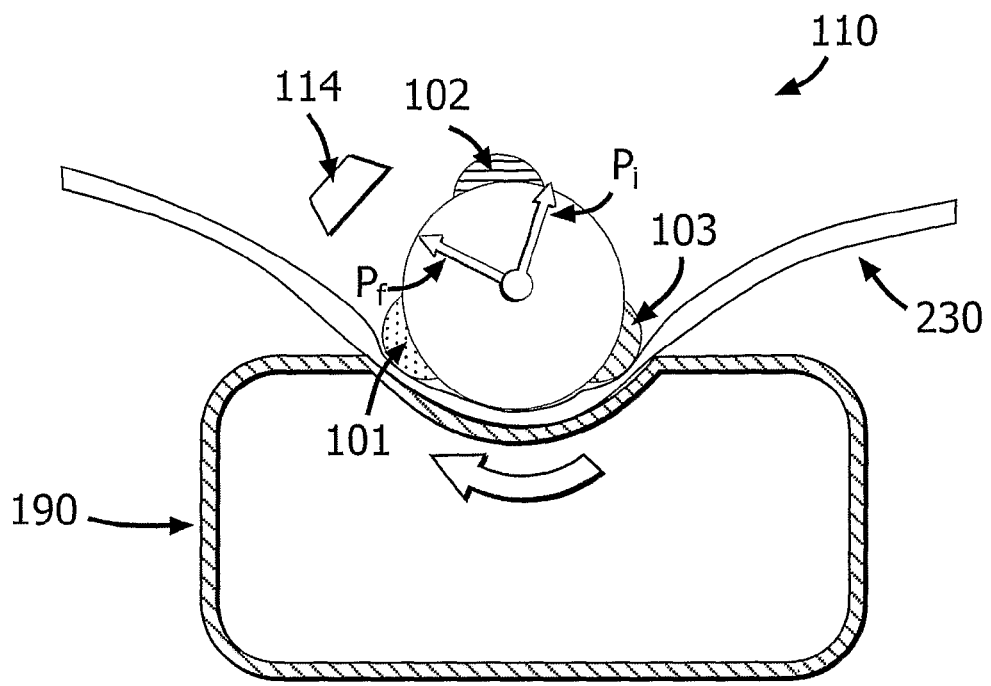
Figure 14K:
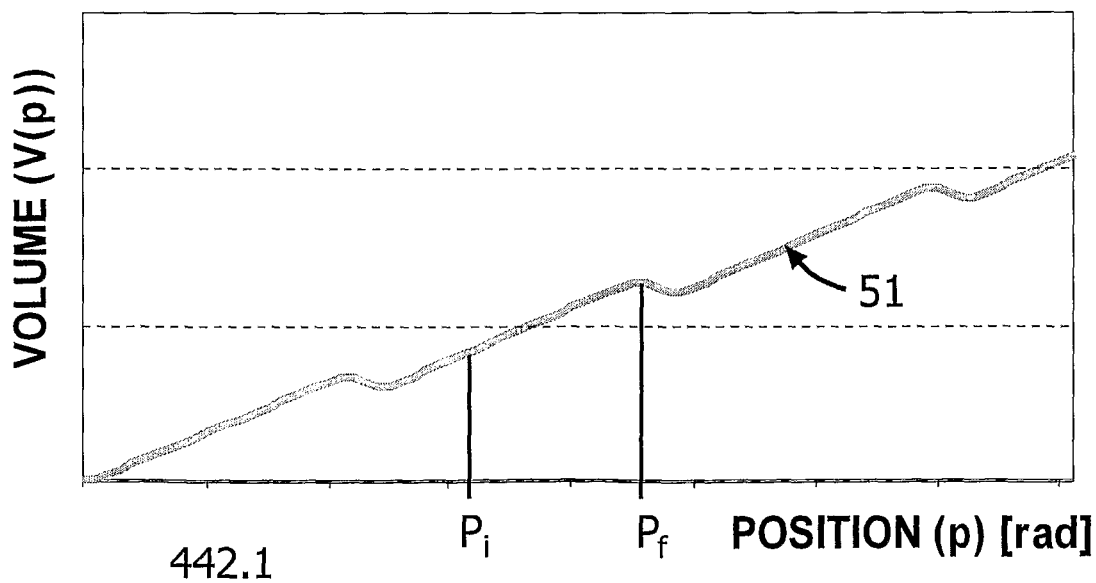
Figure 14L:
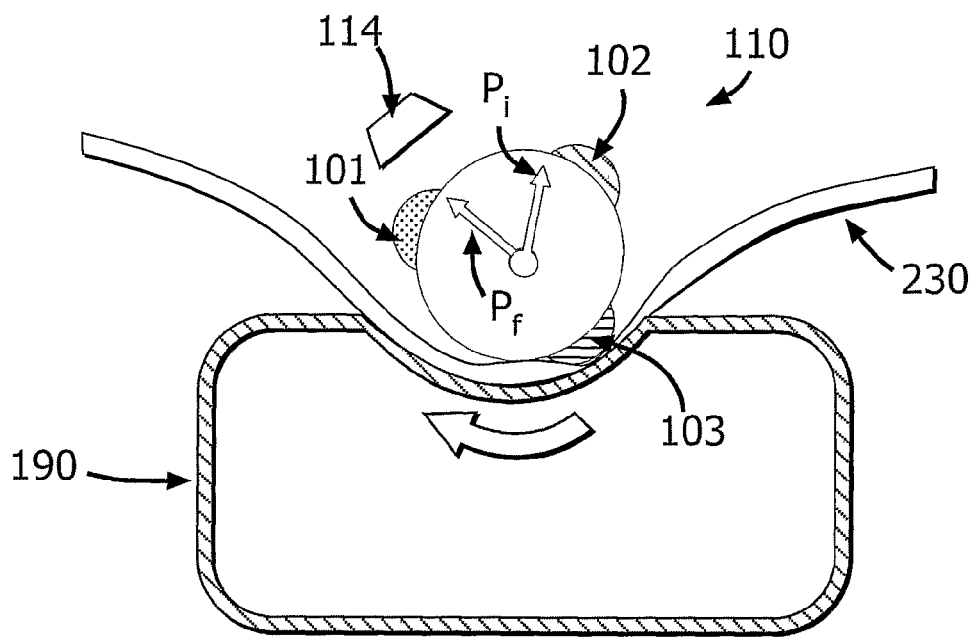
Figure 14M:
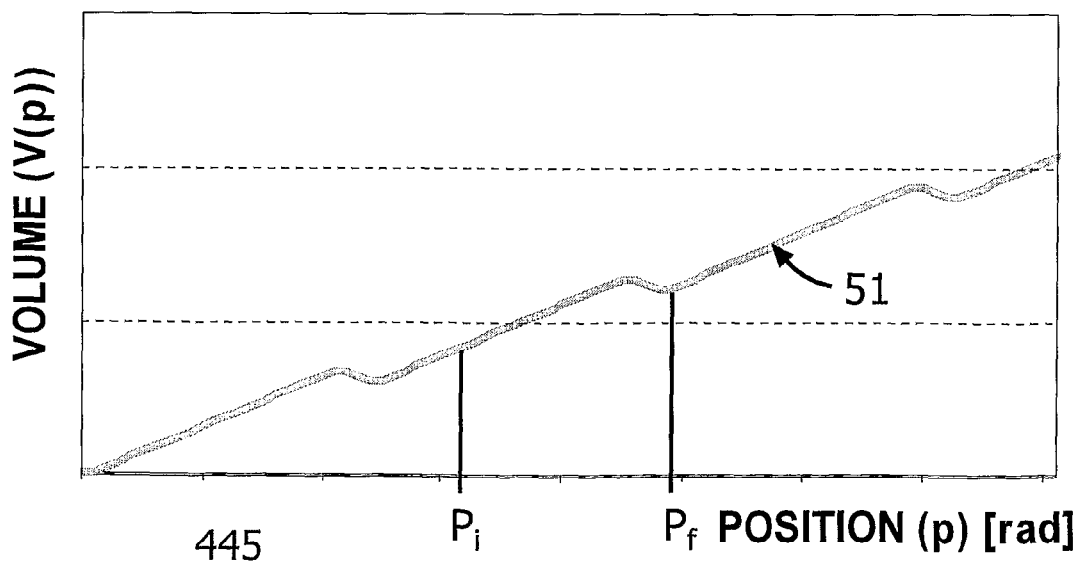
Figure 14N:
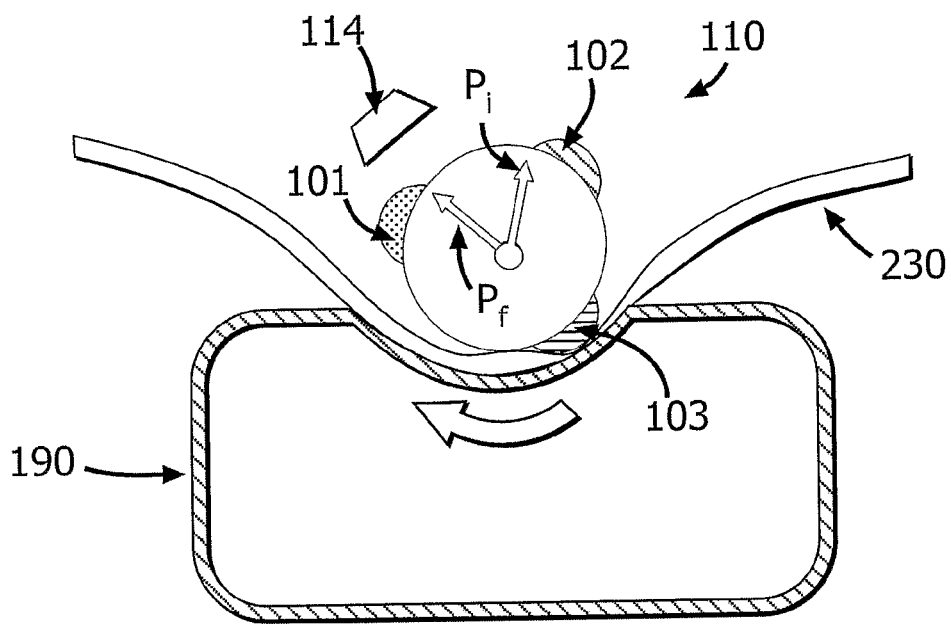
Figure 14O:
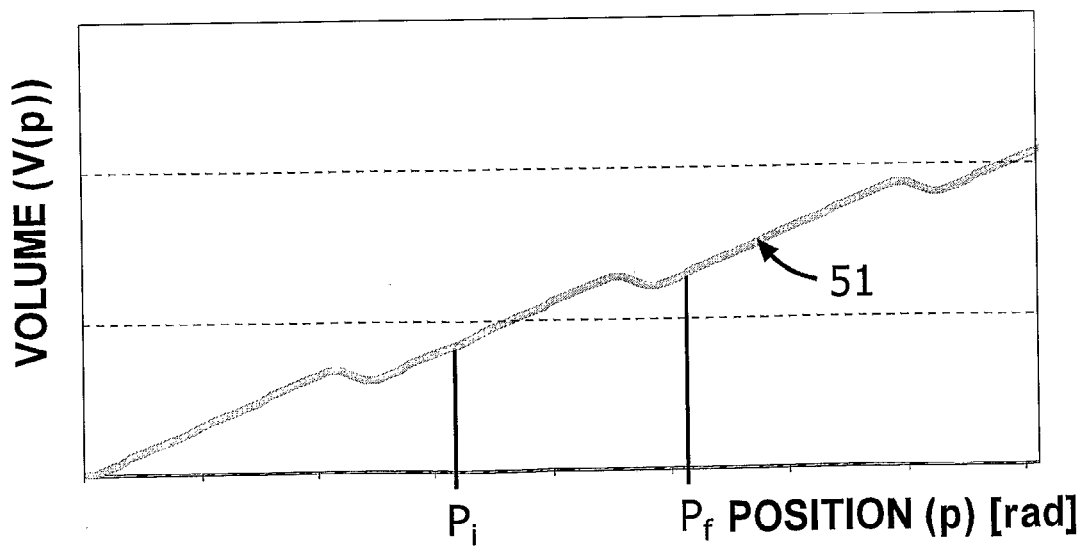

FIGS. 14a-o illustrate examples of fluid delivery using methods described in FIGS. 13a-c and graphically depict the correlation (i.e., the flow characteristic) between the relative position (p) of the rotary wheel (110) and the volume of fluid delivered. FIGS. 14a-d illustrate process (400a), as applied to a dispensing unit (10) having a rotary wheel (110) with four rollers (101, 102, 103, 104), as shown in FIGS. 5a-h. The depictions in FIGS. 14a, 14b, 14c and 14d, numbered (403), (404), (406) and (408), correspond to Steps 403, 404, 406, and 408, respectively, in FIG. 13a. Referring to FIG. 14a, the starting position of the rotary wheel (110) was $p_i$=3π. The dosage to be delivered was V=0.5 μL and the error for previous fluid delivery was Δ=0.02 μL. After the process had started, the targeted position, $p_f$, of the rotary wheel (110) was determined at Step 404 as $p_f$=4π (half a turn of the rotary wheel), as shown in FIG. 14b. Referring to FIGS. 14c and 14d, the rotary wheel (110) was rotated towards the target position ($p_f$=4π) because there was fluid to deliver ($p_f > p_i$). The rotary wheel (110) passed the target position, $p_f$, and stopped 0.1 rad afterward. Sensor (114) measured the present position ($p_i$=4π+0.1=12.7), and ΔV and $V_{total}$ were updated according to V(p) at Step 408 (ΔV=0.01 and $V_{total}$ is increased by 0.5 μL), as the dosage has been delivered ($p_f < p_i$).

FIG. 14e-g illustrates fluid delivery process (400b) described in FIG. 13b, as applied to the dispensing unit (10) having a rotary wheel (110) with three rollers (101, 102, 103). The depictions in FIG. 14e-g, numbered (420), (423) and (425), correspond to Steps 420, 423, and 425, respectively, in FIG. 13b. The initial status of the dispensing unit (10) when the process had started at Step 420 was as follows:

$V_{Tolerance}$=0.02 μL $p_i$=0

$V_{total}$=0 μL  (7)

The dosage (V) to be delivered equals 0.5 μL. Thus, if no backflow occurs, such dosage requires less than half a turn ($p_f$<1.57) of the rotary wheel (110). However, in order to compensate for the backflow, almost a frill turn (1.75π) may be needed. The rotary wheel (110) is rotated until the targeted position $p_f$=2.79 is reached at Step 425, thus, delivering a sufficient amount of fluid (V−(V($p_f$)−V($p_i$))≤$V_{Tolerance}$) at Step 423. Afterwards, Steps 428, 430, and 431 (shown in FIG. 13b) are performed, i.e. updating ΔV, $V_{total}$ and $V_{Tolerance}$, and process (400b) is terminated at Step 432.

FIGS. 14h-o illustrates fluid delivery process (400c) described in FIG. 13c, as applied to the dispensing unit (10) having a rotary wheel (110) with three rollers (101, 102, 103). Each pair of subsequent figures (e.g. FIGS. 14h and 14i or FIGS. 14j and 14k) illustrates a step in the fluid delivery process (400c); the first figure (e.g. FIG. 14h of the pair FIGS. 14h and 14i) shows the position of the rotary wheel, and the second figure (e.g. FIG. 14i of the pair FIGS. 14h and 14i) shows the flow characteristics related to that position. The depictions in FIGS. 14h-o, numbered (441), (442.1), (442.2), and (445), correspond to Steps 441, 442, and 445, respectively, as shown in FIG. 13c. The initial status of the dispensing unit (10) at Step 440, was as follows:

$V_{Tolerance}$=0.02 μL $V_{total}$=127 μL  (8)

The dosage (V) to be delivered equals 0.25 μL.

Referring to FIGS. 14h and 14i, the rotary wheel initial position, $p_i$=0.65, is determined at Step 441 and the rotary wheel (110) is rotated to deliver 0.25 μL. Subsequent to fluid delivery, the rotary wheel's current position is $p_f$=1.9 (V(p)=0.2*(1.9−0.65)=0.25 μL) as shown in FIGS. 14j and 14k. However, at this position there is backflow $$\left(\frac{dV}{dp}(p_f) = k'' = -0.3 < 0\right).$$

Thus, rotary wheel (110) is rotated to position $p_f$=2.09, according to Steps 442 and 445 shown in FIG. 13c. But due to the backflow, the volume delivered is decreased to 0.22 μL, i.e., V(p)=0.2*(1.9−0.65)−0.3*(2−1.9)=0.22 μL, as shown in FIGS. 14l and 14m. Therefore, rotary wheel (110) continues to rotate to $p_f$=2.69 to compensate for the backflow. As indicated in Step 442.2, the rotary wheel (110) is stopped when both of the conditions of Step 442 in FIG. 13c $$\frac{dV}{dp}(p_f) > 0$$

and the dosage V had been delivered) are met, as shown in FIGS. 14n and 14o.

Figure 15:
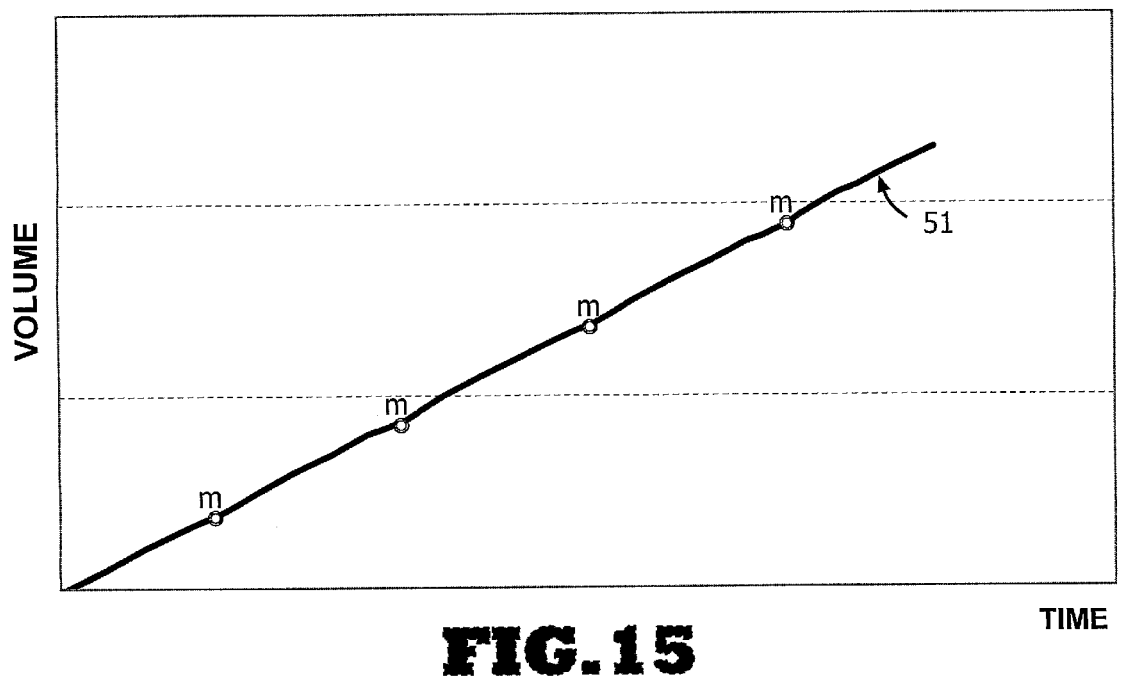
FIG. 15 illustrates a graph of the volume of fluid delivered according to some embodiments.

FIG. 15 illustrates a flow profile (51) of the fluid delivery during one rotation of a rotary wheel (110) having four rollers according to some embodiments. The four nadir points ("m") indicate the phase "d" of a roller where the roller disengages the delivery tube (230). This flow profile can be achieved by adjusting the rotation rate of the driving mechanism (e.g., motor) or the rotary wheel (110) (e.g., adjusting the velocity/speed of rotation). For example, the rotary wheel (110) can be accelerated (increasing velocity/speed) during phases wherein backflow occurs and may be decelerated (decreasing velocity/speed) or maintained constant when backflow does not occur. Thus, a flow profile in accordance with the teachings herein is significantly more uniform and linear than a flow profile employing conventional systems and methods of fluid delivery, as shown in FIG. 6a.

The flow rate and rotation rate adjustment is also beneficial in reduction or prevention of an occurrence or formation of fibrils, aggregations or precipitations when using therapeutic fluid, such as insulin. This adjustment of rotation rate minimizes the period of time during which the backflowing fluid resides in that portion of the delivery tube (230) positioned between the rotary wheel (110) and the stator (190).

Example embodiments of the devices and methods of the present invention have been described herein. As noted elsewhere, these embodiments have been described for illustrative purposes only and are not limiting. Other embodiments are possible and are covered by the invention. Such embodiments will be apparent to persons of ordinary skill in the relevant art(s) based on the teachings contained herein. Thus, the breadth and scope of the disclosure should not be limited by any of the above-described embodiments but should be defined only in accordance with the following claims and their equivalents.

What is claimed is:

1. An ambulatory infusion pump for delivering a desired volume of a therapeutic fluid to a patient's body, the pump including a dispensing unit comprising:
    a reservoir to retain therapeutic fluid;
    a driving mechanism for delivering therapeutic fluid from the reservoir into a patient's body, the driving mechanism including a movable member that moves when therapeutic fluid is being delivered;
    at least one sensor configured to sense a relative radial position of the movable member from an initial position, and generates position sensor signals representing the relative position of the movable member from the initial position, the sensor sensing in the direction from a circumference inward along a radius of the movable member, the at least one sensor comprising a light-emitting source and a light detector, with equally spaced protrusions on the moveable member therebetween intermittently blocking the light emitted by the light-emitting source, and the at least one sensor detects when the protrusions block the light emitted by the light-emitting source and generates the position sensor signals as on-off signals transmitted to a processor; and
    the processor in electrical communication with the at least one sensor and configured with instructions to control the driving mechanism,
    wherein the processor controls the driving mechanism based on the position sensor signals representing the relative position of the movable member from the initial position and at least one flow characteristic of the therapeutic fluid being delivered such that a compensation movement of the movable member is determined and executed to compensate for a change in the flow of therapeutic fluid occurring during operation of the driving mechanism, wherein the compensation movement is an additional positional movement of the moveable member from the relative position to a final position in order to deliver the desired volume of the therapeutic fluid.

2. The pump according to claim 1, further comprising a positive displacement pump.

3. The pump according to claim 1, further comprising a syringe and a propelling plunger.

4. The pump according to claim 1, further comprising:
    a rotary wheel rotatable by the driving mechanism and having at least one roller,
    a stator arranged adjacent to the rotary wheel, and
    a delivery tube in fluid communication with the reservoir, wherein the delivery tube is disposed between the rotary wheel and the stator such that upon rotation of the rotary wheel, a region of the delivery tube is squeezed between the at least one roller and the stator.

5. The pump according to claim 4, wherein the at least one roller is configured to continuously squeeze the region of the delivery tube to prevent therapeutic fluid from flowing in a direction towards the reservoir.

6. The pump according to claim 4, wherein the at least one roller comprises four rollers.

7. The pump according to claim 4, wherein an amount of therapeutic fluid delivered through the delivery tube is determined based on a monitored stator load.

8. The pump according to claim 1, wherein the movable member rotates when therapeutic fluid is delivered, and the at least one sensor monitors the number of rotations of the movable member.

9. The pump according to claim 1, wherein the movable member is selected from the group consisting of an encoder, a shaft, a stator, a gear, a cogwheel, rotary wheel, a roller, and a plunger.

10. The pump according to claim 1, wherein the change in the flow of the therapeutic fluid is periodic.

11. The pump according to claim 1, wherein the driving mechanism further comprises:
    a motor; and
    at least one gear coupled to the motor, and configured to rotate upon application of power from the motor, the gear rotation being monitored by the at least one sensor;
    wherein during activation of the driving mechanism, the gear is rotated at a variable rate resulting in a substantially constant flow rate of therapeutic fluid delivered to the patient's body.

12. The pump according to claim 1, wherein fluid delivery is monitored by at least two sensors.

13. The pump according to claim 1, wherein the processor is further configured to calculate a target position of the movable member based on the sensor signals and on the at least one flow characteristic of the therapeutic fluid being delivered to the patient.

14. The pump according to claim 1, wherein the processor is configured to control the driving mechanism to deliver therapeutic fluid at a basal rate.

15. The pump according to claim 1, wherein:
    the at least one flow characteristic of the therapeutic fluid being delivered includes one or more correlations between the sensor signals and an amount of delivered therapeutic fluid, and
    the amount of delivered therapeutic fluid results from at least one of flow in a forward direction, no flow and backflow.

16. The pump according to claim 1, wherein the driving mechanism, the at least one sensor, and the processor operate in a closed-loop mode.

17. The pump according to claim 1, wherein during operation of the driving mechanism, the flow rate of therapeutic fluid is variable.

18. The pump according to claim 1, wherein the movable member comprises a rotary wheel, and the relative position of the movable member sensed by the at least one sensor is an angular position of the rotary wheel.

19. The pump according to claim 1, wherein the compensation movement of the movable member includes adjusting a speed of the movable member.

20. The pump according to claim 1, wherein the compensation movement of the movable member includes adjusting a rotation rate of the movable member.

21. A method for delivering a desired volume of a therapeutic fluid to a patient's body, the method comprising the steps of:
  operating a driving mechanism to deliver therapeutic fluid to a patient, the driving mechanism including a movable member operatively coupled to a motor;
  receiving position sensor signals corresponding to a relative radial position of the movable member from an initial position, a sensor sensing the relative radial position in the direction from a circumference inward along a radius of the movable member, the sensor comprising a light-emitting source and a light detector, with equally spaced protrusions on the moveable member therebetween intermittently blocking the light emitted by the light-emitting source, and the sensor detects when the protrusions block the light emitted by the light-emitting source and generates the position sensor signals as on-off signals transmitted to a processor;
  determining, via the processor, an amount of therapeutic fluid based on the sensor signals from the initial position and on at least one flow characteristic of the therapeutic fluid; and
  controlling the driving mechanism to deliver the determined amount of therapeutic fluid to the patient and to compensate for a change in the flow of therapeutic fluid occurring during operation of the driving mechanism by providing a compensation movement that is an additional positional movement of the moveable member from the relative position to a final position in order to deliver the desired volume of the therapeutic fluid.

22. The method according to claim 21, wherein operating the driving mechanism is based on comparing the determined amount of therapeutic fluid and a previous amount of therapeutic fluid delivered to the patient.

23. The method according to claim 21, wherein:
  receiving the sensor signals corresponding to the relative position of the movable member comprises:
    receiving a first sensor signal corresponding to a first position of the movable member of the driving mechanism, and
    receiving a second signal corresponding to a second position of the movable member; and
  controlling the driving mechanism comprises:
    adjusting the position of the movable member based on the first sensor signal, the second sensor signal and the at least one flow characteristic of the therapeutic fluid being delivered,
    wherein the at least one flow characteristic varies between receiving the first sensor signal and the second sensor signal.

24. The method according to claim 21, wherein:
  operating the driving mechanism causes periodic delivery of therapeutic fluid; and
  completing a period of the driving mechanism operation results in delivering a first amount of therapeutic fluid.

25. The method according to claim 24, wherein controlling the driving mechanism comprises delivering a second amount of therapeutic fluid to compensate for a change in flow rate of therapeutic fluid occurring during operation of the driving mechanism.

* * * * *